US009206446B2

(12) United States Patent
Lau et al.

(10) Patent No.: US 9,206,446 B2
(45) Date of Patent: Dec. 8, 2015

(54) EXTRACTION OF SOLUBLES FROM PLANT BIOMASS FOR USE AS MICROBIAL GROWTH STIMULANT AND METHODS RELATED THERETO

(75) Inventors: Ming Woei Lau, Maryville, TN (US); Bruce Dale, Mason, MI (US); Venkatesh Balan, East Lansing, MI (US); Shishir Chundawat, Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 1039 days.

(21) Appl. No.: 12/763,102

(22) Filed: Apr. 19, 2010

(65) Prior Publication Data

US 2010/0267999 A1  Oct. 21, 2010

Related U.S. Application Data

(63) Continuation-in-part of application No. 11/897,119, filed on Aug. 29, 2007, now abandoned, and a continuation-in-part of application No. 12/226,850, filed as application No. PCT/US2007/010410 on Apr. 30, 2007, now abandoned.

(60) Provisional application No. 60/796,401, filed on May 1, 2006.

(51) Int. Cl.
*A61K 36/899* (2006.01)
*A61K 36/185* (2006.01)
*C12P 7/10* (2006.01)
*C12N 1/38* (2006.01)
*C12N 9/42* (2006.01)
*C12P 19/02* (2006.01)
*C12P 19/14* (2006.01)
*C12P 21/02* (2006.01)

(52) U.S. Cl.
CPC ... *C12P 7/10* (2013.01); *C12N 1/38* (2013.01); *C12N 9/2434* (2013.01); *C12P 19/02* (2013.01); *C12P 19/14* (2013.01); *C12P 21/02* (2013.01); *C12P 2201/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | |
|---|---|---|
| 2,017,779 A | 10/1935 | Vosburgh |
| 2,548,192 A | 4/1951 | Berg |
| 3,306,006 A | 2/1967 | Urban |
| 3,920,419 A | 11/1975 | Schroeder et al. |
| 4,064,276 A | 12/1977 | Conradsen et al. |
| 4,153,435 A | 5/1979 | Fischer |
| 4,263,744 A | 4/1981 | Stoller |
| 4,356,196 A | 10/1982 | Hultquist |
| 4,370,351 A | 1/1983 | Harper |
| 4,461,648 A | 7/1984 | Foody |
| 4,526,791 A | 7/1985 | Young |
| 4,581,044 A | 4/1986 | Uno et al. |
| 4,589,334 A | 5/1986 | Andersen |
| 4,594,131 A | 6/1986 | Maier |
| 4,600,590 A | 7/1986 | Dale |
| 4,624,805 A | 11/1986 | Lawhon |
| 4,644,060 A | 2/1987 | Chou |
| 4,848,026 A | 7/1989 | Dunn-Coleman et al. |
| 4,986,835 A | 1/1991 | Uno et al. |
| 4,995,888 A | 2/1991 | Beaupre et al. |
| 5,025,635 A | 6/1991 | Rockenfeller et al. |
| 5,037,663 A | 8/1991 | Dale |
| 5,047,332 A | 9/1991 | Chahal |
| 5,114,694 A | 5/1992 | Grotz, Jr. |
| 5,171,592 A | 12/1992 | Holtzapple et al. |
| 5,370,999 A | 12/1994 | Stuart |
| 5,473,061 A | 12/1995 | Bredereck et al. |
| 5,660,603 A | 8/1997 | Elliot et al. |
| 5,736,032 A | 4/1998 | Cox |
| 5,865,898 A | 2/1999 | Holtzapple et al. |
| 5,939,544 A | 8/1999 | Karstens et al. |
| 6,027,552 A | 2/2000 | Ruck et al. |
| 6,106,888 A | 8/2000 | Dale et al. |

(Continued)

FOREIGN PATENT DOCUMENTS

| | | |
|---|---|---|
| AU | 756976 B2 | 1/2003 |
| CA | 2368872 A1 | 10/2000 |

(Continued)

OTHER PUBLICATIONS

Teymouri et al. (Optimization of ammonia fiber explosion (AFEX) treatment parameters for enzymatic hydrolysis of corn stover, Bioresource Technology 96(2005) 2014-2018, publiished Feb. 2005).*

Viable Herbal Solutions (see cited website of www.web.archive.org/web/2000124113842/http://viable-herbal.com/herbology1/herbs42 copyrighted 1996,1997,1998,1999,2000, pp. 1-3).*

"U.S. Appl. No. 12/226,850, Restriction Requirement mailed Jun. 30, 2011", 4 pgs.

"U.S. Appl. No. 12/286,913, Response filed Jul. 15, 2011 to Restriction Requirement mailed Jun. 15, 2011", 3 pgs.

(Continued)

*Primary Examiner* — Chris R Tate
*Assistant Examiner* — Randall Winston
(74) *Attorney, Agent, or Firm* — Clark IP Law, PLC

(57) ABSTRACT

A method for producing a microbial growth stimulant (MGS) from a plant biomass is described. In one embodiment, an ammonium hydroxide solution is used to extract a solution of proteins and ammonia from the biomass. Some of the proteins and ammonia are separated from the extracted solution to provide the MGS solution. The removed ammonia can be recycled and the proteins are useful as animal feeds. In one embodiment, the method comprises extracting solubles from pretreated lignocellulosic biomass with a cellulase enzyme-producing growth medium (such *T. reesei*) in the presence of water and an aqueous extract.

12 Claims, 19 Drawing Sheets

(56) References Cited

U.S. PATENT DOCUMENTS

| | | |
|---|---|---|
| 6,176,176 B1 | 1/2001 | Dale et al. |
| 6,255,505 B1 | 7/2001 | Bijl et al. |
| 6,416,621 B1 | 7/2002 | Karstens |
| 6,425,939 B1 | 7/2002 | Moreau et al. |
| 6,444,437 B1 | 9/2002 | Sporleder et al. |
| 6,524,848 B2 | 2/2003 | McNelly |
| 6,585,807 B2 | 7/2003 | Umino et al. |
| 6,620,292 B2 | 9/2003 | Wingerson |
| 6,872,296 B2 | 3/2005 | Kim |
| 6,893,484 B2 | 5/2005 | Thomas |
| 7,049,485 B2 | 5/2006 | Sticklen et al. |
| 7,187,176 B2 | 3/2007 | Lim et al. |
| 7,250,074 B2 | 7/2007 | Tonkovich et al. |
| 7,371,926 B2 | 5/2008 | Sticklen |
| 7,371,962 B2 | 5/2008 | Zuppero et al. |
| 7,494,675 B2 | 2/2009 | Abbas et al. |
| 7,494,792 B2 | 2/2009 | Warzywoda et al. |
| 7,537,744 B2 | 5/2009 | Benderly et al. |
| 7,585,652 B2 * | 9/2009 | Foody et al. .................. 435/163 |
| 7,771,565 B2 | 8/2010 | Kirov et al. |
| 7,910,338 B2 | 3/2011 | Hennessey et al. |
| 7,910,675 B2 | 3/2011 | Funk et al. |
| 7,915,017 B2 | 3/2011 | Dale |
| 7,937,851 B2 | 5/2011 | Rajagopalan et al. |
| 8,020,342 B2 | 9/2011 | Karpik |
| 8,030,030 B2 | 10/2011 | Varanasi et al. |
| 8,367,378 B2 | 2/2013 | Balan et al. |
| 8,394,177 B2 | 3/2013 | Campbell et al. |
| 8,394,611 B2 | 3/2013 | Dale et al. |
| 8,419,900 B2 | 4/2013 | Baba et al. |
| 8,444,925 B2 | 5/2013 | Baba |
| 8,551,549 B2 | 10/2013 | Zeeck |
| 8,651,403 B2 | 2/2014 | Camp et al. |
| 8,673,031 B2 | 3/2014 | Dale et al. |
| 8,771,425 B2 | 7/2014 | Dale |
| 8,846,123 B2 | 9/2014 | Zeeck |
| 2003/0044951 A1 | 3/2003 | Sporleder et al. |
| 2005/0064577 A1 | 3/2005 | Berzin |
| 2005/0233423 A1 | 10/2005 | Berka et al. |
| 2006/0014260 A1 | 1/2006 | Fan et al. |
| 2006/0130396 A1 | 6/2006 | Werner |
| 2006/0177917 A1 | 8/2006 | Warzywoda et al. |
| 2007/0029252 A1 | 2/2007 | Dunson, Jr. et al. |
| 2007/0031918 A1 | 2/2007 | Dunson, Jr. et al. |
| 2007/0037259 A1 | 2/2007 | Hennessey et al. |
| 2007/0113736 A1 | 5/2007 | Bandosz |
| 2007/0192900 A1 | 8/2007 | Sticklen |
| 2007/0202214 A1 | 8/2007 | Lewis et al. |
| 2007/0227063 A1 | 10/2007 | Dale et al. |
| 2007/0287795 A1 | 12/2007 | Huda et al. |
| 2008/0008783 A1 | 1/2008 | Dale |
| 2008/0057555 A1 | 3/2008 | Nguyen |
| 2008/0087165 A1 | 4/2008 | Wright et al. |
| 2008/0115415 A1 | 5/2008 | Agrawal et al. |
| 2008/0171297 A1 | 7/2008 | Reynolds et al. |
| 2008/0229657 A1 | 9/2008 | Senyk et al. |
| 2008/0256851 A1 | 10/2008 | Lumb |
| 2008/0264254 A1 | 10/2008 | Song et al. |
| 2008/0280236 A1 | 11/2008 | Wright |
| 2009/0011474 A1 | 1/2009 | Balan et al. |
| 2009/0042259 A1 | 2/2009 | Dale et al. |
| 2009/0049748 A1 | 2/2009 | Day et al. |
| 2009/0053770 A1 | 2/2009 | Hennessey et al. |
| 2009/0053771 A1 | 2/2009 | Dale et al. |
| 2009/0061486 A1 | 3/2009 | Edwards et al. |
| 2009/0087898 A1 | 4/2009 | Haase et al. |
| 2009/0093027 A1 | 4/2009 | Balan et al. |
| 2009/0099079 A1 | 4/2009 | Emalfarb et al. |
| 2009/0123361 A1 | 5/2009 | Johannessen et al. |
| 2009/0178671 A1 | 7/2009 | Ahring |
| 2009/0221042 A1 | 9/2009 | Dale et al. |
| 2009/0230040 A1 | 9/2009 | Limcaco |
| 2009/0313976 A1 | 12/2009 | Johannessen et al. |
| 2009/0318670 A1 | 12/2009 | Dale et al. |
| 2010/0159521 A1 | 6/2010 | Cirakovic et al. |
| 2010/0279361 A1 | 11/2010 | South et al. |
| 2011/0192559 A1 | 8/2011 | Venkatesh et al. |
| 2011/0201091 A1 | 8/2011 | Dale |
| 2011/0290114 A1 | 12/2011 | Campbell et al. |
| 2011/0300269 A1 | 12/2011 | Dale et al. |
| 2012/0064574 A1 | 3/2012 | Tokuyasu et al. |
| 2012/0071308 A1 | 3/2012 | Sekar |
| 2012/0085505 A1 | 4/2012 | Sabourin |
| 2012/0125548 A1 | 5/2012 | Cohen |
| 2012/0125551 A1 | 5/2012 | Cohen et al. |
| 2012/0187228 A1 | 7/2012 | Camp et al. |
| 2012/0325202 A1 | 12/2012 | Dale |
| 2013/0196398 A1 | 8/2013 | Bals et al. |
| 2013/0217073 A1 | 8/2013 | Chundawat et al. |
| 2013/0247456 A1 | 9/2013 | Dale et al. |
| 2013/0280762 A1 | 10/2013 | Dale et al. |
| 2013/0289268 A1 | 10/2013 | Teymouri et al. |
| 2014/0038243 A1 | 2/2014 | Balan et al. |
| 2014/0227757 A1 | 8/2014 | Jin et al. |

FOREIGN PATENT DOCUMENTS

| | | |
|---|---|---|
| CA | 2573046 A1 | 1/2006 |
| CA | 2610797 A1 | 12/2006 |
| CA | 2752604 A1 | 8/2010 |
| CA | 2762985 C | 7/2013 |
| CA | 2650860 C | 9/2013 |
| CA | 2737704 C | 11/2013 |
| CN | 101223273 A | 7/2008 |
| CN | 102597247 A | 7/2012 |
| CN | 102939388 A | 2/2013 |
| DE | 20301645 | 4/2003 |
| EP | 0144930 A2 | 6/1985 |
| EP | 1247781 A2 | 10/2002 |
| EP | 1533279 A1 | 5/2005 |
| EP | 1690944 A1 | 8/2006 |
| EP | WO2008/020901 A2 | 2/2008 |
| GB | 1310835 A | 3/1973 |
| GB | 1381728 A | 1/1975 |
| GB | 2122864 A | 1/1984 |
| IN | 249187 | 10/2011 |
| IN | 9645DELNP2011 A | 2/2013 |
| JP | 2008-161125 A | 7/2008 |
| JP | 2008-535664 A | 9/2008 |
| JP | 2011160753 A | 8/2011 |
| RU | 2215755 C1 | 11/2003 |
| WO | 8500133 A1 | 1/1985 |
| WO | 00/61858 A1 | 10/2000 |
| WO | 01/32715 A1 | 5/2001 |
| WO | 0237981 A2 | 5/2002 |
| WO | 2004/033920 A1 | 4/2004 |
| WO | 2006/055362 A1 | 5/2006 |
| WO | 2006/128304 A1 | 12/2006 |
| WO | 2007/005918 A2 | 1/2007 |
| WO | 2007/005918 A3 | 8/2007 |
| WO | WO-2007130337 A1 | 11/2007 |
| WO | WO-2007227063 | 11/2007 |
| WO | WO-2008020901 A2 | 2/2008 |
| WO | 2008/020901 A3 | 7/2008 |
| WO | 2008/114139 A2 | 9/2008 |
| WO | 2008/114139 A3 | 12/2008 |
| WO | WO-2009045527 A1 | 4/2009 |
| WO | 2010/098408 A1 | 9/2010 |
| WO | 2010/121348 A1 | 10/2010 |
| WO | 2010/135679 A1 | 11/2010 |
| WO | 2010147218 A1 | 12/2010 |
| WO | 2011028543 A2 | 3/2011 |
| WO | WO-2011028543 A2 | 3/2011 |
| WO | 2011/046818 A2 | 4/2011 |
| WO | 2011/028543 A3 | 6/2011 |
| WO | 2011/080154 A1 | 7/2011 |
| WO | 2011/125056 A1 | 10/2011 |
| WO | 2011/133571 A2 | 10/2011 |
| WO | 2011133571 A3 | 10/2011 |
| WO | 2012/012594 A1 | 1/2012 |
| WO | 2012071312 A2 | 5/2012 |
| WO | 2012/088429 A2 | 6/2012 |
| WO | 2013/106113 A2 | 7/2013 |
| WO | 2013/131015 A1 | 9/2013 |

(56) References Cited

FOREIGN PATENT DOCUMENTS

| WO | 2013/106133 A3 | 10/2013 |
| WO | 2013/163571 A2 | 10/2013 |
| WO | 2013/163571 A3 | 3/2014 |

OTHER PUBLICATIONS

"Canadian Application Serial No. 11/901,336, Response filed Jun. 29, 2011 to Office Action mailed May 12, 2011", 2 pgs.
Balan, V., et al., "Mushroom spent straw: a potential substrate for an ethanol-based biorefinery", J Ind Microbiol Biotechnol., 35(5), (May 2008), 293-301.
Baldrian, P, et al., "Variability of laccase activity in the white-rot basidiomycetePleurotus ostreatus", Folia Microbiologica, 47, (2002), 385-90.
Chahal, D S, "Bioconversion of hemicelluloses into useful products in an integrated process for food/feed and fuel (ethanol) production from biomass", Research Org, Univ. de Quebec, Canada., (1984), 355-61.
Chang, Shu-Ting, "The World Mushroom Industry: Trends and Technological Development", International Journal of Medicinal Mushrooms, 8(4), (2006), 297-314.
Christian, V., et al., "Degradation of xenobiotic compounds by lignin-degrading white-rot fungi: enzymology and mechanisms involved", Indian Journal of Experimental Biology, 43, (Apr. 2005), 301-312.
Cohen, "Biotechnological applications and potential of wood-degrading mushrooms of the genus *Pleurotus*", Appl Microbiol Biotechnol, 58, (2002), 582-94.
De Ferrer, B Sulbaran, et al., "No. 6. Sugar production from rice straw", Arch. Latinoam. Prod. Anim., 5(Supl.1), (1997), 112-114.
Ferrer, A, et al., "Increasing nutrient availability of feather meal for ruminants and non-ruminants using an ammonia pressurisation/depressurisation process", Journal of the Science of Food and Agriculture, 79, (May 1999), 828-32.
Gollapalli, L. E, et al., "Predicting digestibility of ammonia fiber explosion (AFEX)-treated rice straw", Appl Biochem Biotechnol., 98-100, (2002), 23-35.
Houghton, T. P, et al., "Fungal upgrading of wheat straw for straw-thermoplastics production", Appl Biochem Biotechnol., 113-116, (2004), 71-93.
Israelides, Cleanthes, "Bio-technologies of recycling agro-industrial wastes for the production of commercially important fungal polysaccharides and mushrooms.", Biotechnol Genet Eng Rev, 20, (2003), 247-59.
Karunanandaa, K., et al., "Botanical fractions of rice straw colonized by white-rot fungi: changes in chemical composition and structure", Animal Feed Science and Technology, 55(3), (Oct. 1995), 179-99.
Keller, Fred A, et al., "Microbial pretreatment of biomass: potential for reducing severity of thermochemical biomass pretreatment", Appl Biochem Biotechnol., 105-108, (Spring, 2003), 27-41.
Martinez, Angel T, et al., "Biodegradation of lignocellulosics: microbial, chemical, and enzymatic aspects of the fungal attack of lignin", International Microbiology, 8, (2005), 195-204.
Obodai, "Comparative study on the growth and yield of *Pleurotus ostreatus* mushroom on different lignocellulosic by-products", J Ind Microbiol Biotechnol, 30, (2003), 146-9.
O'Connor, J. J, "Ammonia explosion pulping—a new fiber separation process", Tappi, 55(3), (Mar. 1972), 353-358.
Poppe, J, "Use of agricultural waste materials in the cultivation of mushrooms", In Science and cultivation of edible fungi. Proceedings of the 15th International Congress on the Science and Cultivation of Edible Fungi, Maastricht, Netherlands, May 15-19, 2000., 9-23.
Sanchez, Alfonso, et al., "Biodegradation of viticulture wastes by Pleurotus: a source of microbial and human food and its potential use in animal feeding", J Agric Food Chem., 50(9), (Apr. 24, 2002), 2537-42.
Sarikaya, Ayda, et al., "Solid-state fermentation of lignocellulosic plant residues from Brassica napus by Pleurotus ostreatus", Appl Biochem Biotechnol., 82(1), (Oct. 1999), 1-15.
Singh, Anshu, et al., "Composting of a crop residue through treatment with microorganisms and subsequent vermicomposting", Bioresouce Technology, 85, (2002), 107-11.
Taniguchi, Masayuki, et al., "Evaluation of pretreatment with Pleurotus ostreatus for enzymatic hydrolysis of rice straw", Journal of Bioscience and Bioengineering, 100(6), (Dec. 2005), 637-643.
Teymouri, Farzaneh, et al., "Optimization of the ammonia fiber explosion (AFEX) treatment parameters for enzymatic hydrolysis of corn stover", Bioresource Technology, 96, (2005), 2014-18.
Turner, N D, et al., "Disruption of forage structure with an ammonia fiber explosion process", Proceedings, Western Section, American Society of Animal Science, 41, (1990), 794-97.
Williams, B C, et al., "An initial assessment of spent mushroom compost as a potential energy feedstock", Bioresource Technology, 79, (2001), 227-30.
Wyman, Charles E, et al., "Comparative sugar recovery data from laboratory scale application of leading pretreatment technologies to corn stover", Bioresource Technology, 96, (2005), 2026-32.
Wyman, Charles E, et al., "Coordinated development of leading biomass pretreatment technologies", Bioresour Technol., 96(18), (Dec. 2005), 1959-66.
Zhang, Ruihong, et al., "Oyster mushroom cultivation with rice and wheat straw", Bioresour Technol., 82(3), (May 2002), 277-84.
"U.S. Appl. No. 11/729,632, Amendment "A" filed Sep. 11, 2009 to Office Action mailed May 6, 2009", 9 pgs.
"U.S. Appl. No. 11/729,632, Interview Summary and Response B, filed Oct. 30, 2009 to Office Action mailed May 6, 2009", 9 pgs.
"U.S. Appl. No. 11/729,632, Non Final Office Action mailed May 6, 2009", 4 pgs.
"U.S. Appl. No. 11/897,119, Restriction Requirement mailed Sep. 30, 2011", 6 pgs.
"U.S. Appl. No. 12/226,763, Non Final Office Action mailed Aug. 22, 2011", 13 pgs.
"U.S. Appl. No. 12/229,225, Non Final Office Action mailed Aug. 16, 2011", 6 pgs.
"U.S. Appl. No. 12/286,913, Non Final Office Action mailed Sep. 28, 2011", 7 pgs.
"European Application Serial No. 11162906.9, Partial EP Search mailed Aug. 23, 2011", 9 pgs.
"Indian Application Serial No. 5933/CHENP/2008, Response filed Sep. 14, 2011 to Office Action mailed Oct. 14, 2010", 11 pgs.
Cen, P, et al., "Production of Cellulase by Solid-State Fermentation", In Tsao (editor) Recent Progress in Bioconversion, ISSN 0724-6145, ISBN 3-540-65577-8, (1999), 70-92.
Chahal, D S, "Bioconversion of Hemicelluloses into Useful Products in an Integrated Process for Fool/Feed and Fuel (Ethanol) Production from Biomass", Hemicellulose Bioconversion, Biotechnol. Bioeng. Symp., (1984), 425-433.
Chahal, P. S, et al., "Production of cellulase in solid-state fermentation with Trichoderma reesei MCG 80 on wheat straw", Applied Biochemistry and Biotechnology, 57/5(8), XP008054568, ISSN : 0273-2289, DOI : 10.1007/ BF029417246, (Jan. 1, 1996), 433-442.
Chang, Shu-Ting, "The World Mushroom Industry: Trends and Technological Development", International Journal of Medicinal Mushrooms, (2006), 297-314.
Ferrer, Sulbaran B, et al., "Sugar Production from Rice Straw", Suppl. 1, Arch Latinoam Prod Anim 5, (1997), 112-114.
Jain, A, et al., "Effect of Ammonia Pretreatment on Switchgrass for Production of Cellulaseusing Trichoderma reesei Rut C-30", 31st Symposium on Biotechnology for Fuels and Chemicals 5_34, Poster session 2, Retrieved from the Internet at http://sim.confex.com/sim/31st/techprogram/P8269.htm [retrieved on Aug. 11, 2011], (May 4, 2009), 1 pg.
Lynd, L. R, et al., "Microbial cellulose utilization fundamentals and biotechnology", Microbiology and Molectular Biology Reviews, American Society for Microbiology, 66(3), XP002551605 ISSN: 1092-2172, 00110.1128/MMBR.66.3.506-577.2002, (Sep. 1, 2002), 506-739.
Nwodo, S. Chinedu, et al., "Xylanase Production of Aspergillus niger and Penicillium chrysogenum from Ammonia Pretreated Cellulosic Waste", Research Journal of Microbiology, 3(4) [Online ] Retrieved

(56) References Cited

OTHER PUBLICATIONS from the Internet at http://scialert.net/qredirect.php?doi=jm.2008.246.253&linkid=pdf [retrieved on Aug. 10, 2011], (Apr. 1, 2008), 246-253.
Singhania, R. R, et al., "Advancement and comparative profiles in the production techno logies using solid-state and submerged fermentation for microbial cellulases", Enzyme and Microbial Technology, 46(7), Stoneham MA [Online] XP027038189, ISSN: 0141-0229, paragraphs 4, 4.1, 4.2, Table 3, (Mar. 31, 2010), 541-49.
Warzywoda, M, et al., "Production and Characterization of Cellulolytic Enzymes from Trichoderma reesei Grown on Various Carbon Sources", Warzywoda, M. et al. (1992) Bioresource Technol. 39, 125-130, 125-130.
Adaoa, P. et al., "Compression Characteristics of Selected Ground Agricultural Biomass", Agricultural Engineering International: The CIGR eJournal, Manuscript 1347, vol. XI, (Jun. 2009), 19 pgs.
Kaliyan, N. et al., "Roll Press Briquetting and Pelleting of Corn Stover and Switchgrass", Transactions of the ASABE, vol. 52, No. 2, (2009), 543-555.
Lin, K et al., "Chemical Engineer's Handbook", 5th Supp. Edition 1973 Chapter 4 McGraw-Hill N.Y, (1973).
Miller, Norman "Re: Commitment Letter "Phase I Biomass Enhanced Refined Lignite Demonstration Project"", http://www.nd.gov/ndic/renew/meeting0903/r005-a-prop.pdf,(Dec. 2008),24 pgs.
U.S. Appl. No. 11/729,632, Response filed Sep. 11, 2009 to Non Final Office Action mailed May 6, 2009, 9 pgs.
U.S. Appl. No. 12/229,225 Response filed Nov. 15, 2011 to Non Final Office Action mailed Aug. 16, 2011, 12 pgs.
U.S. Appl. No. 12/286,913, Response filed Dec. 28, 2011 to Non Final Office Action mailed Sep. 28, 2011, 13 pgs.
U.S. Appl. No. 12/226,763, Response filed Dec. 21, 2011 to Non Final Office Action mailed Aug. 22, 2011, 11 pgs.
U.S. Appl. No. 12/226,763, Final Office Action mailed Jan. 10, 2012, 16 pgs.
U.S. Appl. No. 12/229,225, Final Office Action Mailed Jan. 6, 2012, 7 pgs.
U.S. Appl. No. 12/976,344, Notice of Allowance mailed Feb. 23, 2012, 7 pgs.
U.S. Appl. No. 11/729,632, Notice of Allowance mailed Nov. 16, 2009, 7 pgs.
U.S. Appl. No. 12/229,225, Response filed Nov. 15, 2011 to Non Final Office Action mailed Aug. 16, 2011, 12 pgs.
U.S. Appl. No. 12/286,913, Non Final Office Action mailed Mar. 1, 2012, 7 pgs.
Canadian Application Serial No. 2,650,860, Office Action mailed Oct. 24, 2011, 3 pgs.
Chinese Application Serial No. 200780025394.4, Office Action mailed Oct. 13, 2011, (with English translation), 11 pgs.
European Application Serial No. 10778488.6, Office Action mailed Dec. 30, 2011, 2 pgs.
European Application Serial No. 11162906.9, Office Action mailed Jan. 16, 2012, 2 pgs.
International Application Serial No. PCT/US2010/046525, Search Report mailed Apr. 29, 2011, 5 pgs.
International Application Serial No. PCT/US2010/046525, Written Opinion mailed Apr. 29, 2011, 4 pgs.
"U.S. Appl. No. 11/901,336 Office Action Response Filed Jun. 29, 2011", 2.
Balan, "Mushroom spent straw: a potential substrate for an ethanol-based biorefinery", J Ind. Microbio Technol, 35, (2008), 293-301.
Chang, Shu-Ting, "The world mushroom industry: trends and technical development", International Journal of Medicinal Mushrooms, 8, (2006), 297-314.
Christian, V, et al., "Degradation of xenobiotic compounds by lignin-degrading white-rot fungi: enzymology and mechanisms involved", Indian Journal of Experimental Biology, 43, (Apr. 2005), 301-312.
Gollapalli, L. E, et al., "Predicting digestibility of ammonia fiber explosion (AFEX) treateii rice straw", Appl Biochem Biotech, (2002), 98-100.
Houghton, et al., "Fungal upgrading of wheat straw for straw-thermoplastics production", Applied Biochemistry and Biotechnology, vol. 113-116, (2004), 71-93.
Karunanandaa, "Botanical fractions of rice straw colonized by white-rot fungi: changes in chemical composition and structure", Animal Feed Science and Technology, 55(3), (Oct. 1995), 179-99.
Kellar, Fred A, et al., "Microbial pretreatment of biomass", Applied Biochemical Biotechnology, (Spring 2003), 27-41.
O'Connor, "Ammonia explosion pulping—a new fiber separation process", Tappi, 55(3), (Mar. 1972).
Sanchez, Alfonso, "Biodegradation of Viticulture Wastes by Pleurotus: A Source of Microbial and Human Food and Its Potential Use in Animal Feeding", Journal of Agriculture and Food Chemistry, (2002), 2537-42.
Sarikaya, Ayda, et al., "Solid-state fermentation of lignocellulosic plant residues from Brassica napus by Pleurotus ostreatus", Applied Biochemistry and Biotechnology, (1999), 1-15.
Wyman, Charles E, et al., "Coordinated development of leading biomass pretreatment technologies", Bioresource Technology, 96, (2005), 1959-66.
Zhang, Ruihong, et al., "Oyster mushroom cultivation with rice and wheat straw", Bioresource Technology, 82, (2002), 277-84.
"U.S. Appl. No. 11/901,336, Response to Restriction Requirement mailed Mar. 11, 2010", 9 pgs.
"U.S. Appl. No. 11/901,336, Non Final Office Action mailed Apr. 27, 2010", 10 pgs.
"U.S. Appl. No. 11/901,336, Notice of Allowance mailed Aug. 24, 2010", 5 pgs.
"U.S. Appl. No. 11/901,336, Response to Non Final Office Action mailed Apr. 27, 2010", 11 pgs.
"U.S. Appl. No. 11/901,336, Restriction Requirement mailed Mar. 11, 2010", 9 pgs.
"U.S. Appl. No. 12/214,687, Non Final Office Action mailed Jun. 2, 2011", 6 pgs.
"U.S. Appl. No. 12/226,763, Preliminary Amendment filed Dec. 16, 2008", 4 pgs.
"U.S. Appl. No. 12/229,225, Response Filed Jun. 6, 2011 to Restriction Requirement Received May 5, 2011", 10 pgs.
"U.S. Appl. No. 12/229,225, Restriction Requirement mailed May 5, 2011", 6 pgs.
"U.S. Appl. No. 12/286,913, Restriction Requirement mailed Jun. 15, 2011", 4 pgs.
"U.S. Appl. No. 12/976,344, Preliminary Amendment filed Apr. 27, 2011", 10 pgs.
"Australian Application Serial No. 2007248736, Australian Office Action mailed Dec. 1, 2009", 2 pgs.
"Australian Application Serial No. 2007248736, Response filed Mar. 24, 2010 to Australian Office Action mailed Dec. 1, 2009", 7 pgs.
"Canadian Application Serial No. 2,650,860, Office Action mailed May 12, 2011", 2 pgs.
"Energy Policy Act of 2005", Sec. 1501, 109th Cong., 1st Sess, (2005), 11 pgs.
"European Application Serial No. 07776479.3, Amendment (new claims) dated Dec. 16, 2010", 9 pgs.
"European Application Serial No. 07776479.3, Extended European Search Report mailed May 26, 2010", 6 pgs.
"From Niche to Nation: Ethanol Industry Outlook 2006", Renewable Fuels Association Washington DC, (2006), 24 pgs.
"Fuel Ethanol Industry Bio-Refineries and Production Capacity,", U.S. Renewable Fuels Association website, (Accessed Nov. 19, 2008).
"Indian Application Serial No. 5933/CHENP/2008, Office Action mailed Oct. 29, 2010", English translation, 2 pgs.
"International Application Serial No. PCT/US2007/010410, International Search Report mailed Jun. 10, 2008", 1 pg.
"International Application Serial No. PCT/US2007/010410, International Written Opinion mailed Jun. 10, 2008", 4 pgs.
"International Application Serial No. PCT/US2007/010410, Preliminary Report on Patentability mailed Dec. 12, 2008", 5 pgs.
"International Application Serial No. PCT/US2007/010415, Preliminary Report on Patentability mailed Aug. 1, 2008", 7 pgs.
"International Application Serial No. PCT/US2007/10415, International Search Report mailed Oct. 11, 2007", 2 pgs.

(56) References Cited

OTHER PUBLICATIONS

"International Application Serial No. PCT/US2007/10415, Written Opinion mailed Sep. 17, 2007", 4 pgs.
"International Application Serial No. PCT/US2008/011488, International Search Report mailed Jan. 8, 2009", 1 pg.
"International Application Serial No. PCT/US2008/011488, International Written Opinion mailed Jan. 8, 2009", 5 pgs.
Bahar, H, et al., "Splitting tendency of cellulosic fibers", Part 2: Effects of fiber swelling in alkali solution Cellulose, 13, (2006), 403-409.
Beale, C V, "Leaf photosynthesis in the C4 grass Miscanthus x giganteus, growing in the cool temperate climate of southern England", Journal of Experimental Botany, 47, (1996), 267-273.
Belyea, Ronald L, et al., "Element Concentrations of Dry-Grind Corn-Processing Streams", Appl. Biochem. Biotechnol. 134, (2006), 13-128.
Boluk, Y, "Acid-base interactions and swelling of cellulose fiber in organic liquids", Cellulose, 12, (2005), 577-593.
Bothast, R. J, et al., "Biotechnological processes for conversion of com into ethanol", App, Microbiol Biotechnol., 67, (2005), 19-25.
Chundawat, S PS, et al., "Effect of Particle Size Based Seperation of Milled Corn Stover on AFEX Pretreatment and Enzymatic Digestibility", Bioeng. Biotechnol, (2007), 219-231.
Chundawat, Shishir Pratap Singh, "Ultrastructural and physicochemical modifications within ammonia treated lignocellulosic cell walls and their influence on enzymatic digestibility", Ph.D., Michigan State University, (2010), 469 pgs.
Clifton-Brown, J C, et al., "Performance of 15 Miscanthus genotypes at five sites in Europe", Agronomy J., 93, (2001), 1013-1019.
De Vrije, T, et al., "Pretreatment of miscanthus for hydrogen production by Thermotoja elfi", International Journal of Hydrogen Economy, 27, (2005), 1381-1390.
Eggeman, Tim I, et al., "Process and Economic Anaylsis of Pretreatment Technologies", Bioresource Technology, 96, (2005), 2019-2025.
Felix, A., et al., "In Vitro and In Vivo Digestibility of Soya-Bean Straw Treated with Various Alkalis", Anim. Prod, 51, (1990), 47-61.
Foster, B L, et al., "Enzymatic hydrolosis of ammonia treated sugar beet pulp", Apple Biochem Biotechnol, vol. 91-93, (2001), 269-282.
Gray, Kevin A, et al., "Bioethanol", Current Opinion in Chemical Biology, 10, (2006), 141-146.
Hahn-Hagerdal, B., et al., "Bio-ethanol—the fuel of tomorrow from the residues of today", Trends in Biotech., vol. 24, No. 12, (2006), 549-556.
Heaton, E, et al., "A quantitative review comparing the yeilds of two canidate C-4 perennial biomass crops in relation to nitrogen, temperature and water", Biomass and Bioenergy, 27, (2004), 21-30.
Heaton, E A, et al., "Miscanthus for Renewable Energy Generation: European Union Experience and Projections for Illinois", Mitigation and Adaptation Strategies for Global Change, (2004), 433-451.
Jeoh, T, et al., "Cooperative and competative binding in synergistic mixtures of Thermobifidia furca cellulases Cel5A, Cel6B, and Cel9A", Biotechnol Prog., 18, (2002), 760-769.
Kamm, B., et al., "Principles of Biorefineries", Appl Mircobiol Biotechnol., 64, (2004), 137-145.
Kim, S B, et al., "Enhancement of the enzymatic digestility of waste newspaper using Tween", Appl. Biochem. Biotechnol., 129-132, (2006), 486-495.
Knauf, M., et al., "Lignocellulosic Biomass Processing: A Perspective", Int. Sugar J.,106, (2004), 147-150.
Kudra, T., et al., "Superheating Steam Drying", Advanced Drying Technologies, New York, NY : Marcel Dekker, Inc., (2002), 81-111.
Mantanis, G I, et al., "Swellin of compressed cellulose fiber webs in organic liquids", Cellulose, vol. 2, (1995), 1-22.
Mosier, N, et al., "Features of promising technologies for pretreatment of lignocellulosic biomass", Biosource Technology, 96(6), (Apr. 2005), 673-686.
Ohara, H., "Biorefinery", Appl. Microbiol Biotechnol., 62, (2003), 474-477.
Pandey, A, et al., "Economic utilization of crop residues for value addition: a futuristic approach", J. Sci. Ind. Res., vol. 59, (2000), 12-22.
Ragauskas, A J, et al., "The Path Forward for Biofuels and Biomaterials", Science, vol. 311, (2006), 484-489.
Rajagopalan, S., et al., "Enhancing Profitability of Dry Mill Ethanol Plants", Appl. Biochem, Biotechnol, 120, (2004), 37-50.
Rausch, K. D, et al., "The Future of Co-products from Corn Processing", AppL Biochem. Biotechnol. 128, (2006), 47-86.
Saha, B. C, "Hemicellulose Bioconversion", J. Ind Microbiol Biotechnol., 30, (2003), 279-291.
Sun, Y., et al., "Hydrolysis of Lignocellulosic materials for ethanol Production", Bioresource Rechnology, 83, (2002), 1-11.
Uraki, Y, et al., "Boday temperature-responsive gels derived of hydroxypropylcellose bearing lignin II: Adsorption and release behavior", Cellulose, 13, (2006), 225-234.
Waiss, Jr, A. C, et al., "Improving Digestibility of Straws for Ruminant Feed by Aqueous Ammonia", Journal of Animal Science; 35(1), (1972), 109-112.
Wheals, A. E., et al., "Fuel ethanol after 25 years", TIBTECH, 17, (1999), 482-487.
Ye, D, et al., "Improving accessibility and reactivity of cellulose of annual plants for the synthesis of methylcellulose", Cellulose, 12, (2005), 507-515.
Zhang, Y H, et al., "A transition from cellulose swelling to cellulose dissolution by o-phosphoric acid: evidence from enzymatic hydrolysis and supramolecular structure", Biomacromolecules, 7(2), (Feb. 2006), 644-8.
Zhang, Y-H. P, et al., "Toward an Aggregated Understanding of Enzymatic Hydrolysis of Cellulose: NonComplexed Cellulase Systems", Biotechnol. Bioeng., 88, (2004), 797-824.
Sheridan, B.A. et al., "Assessment of the Influence of Media Particle Size on the Biofiltration of Odorous Exhaust Ventilation Air From a Piggery", Bioresource Technology, vol. 84, 2002, 129-143.
Sulbaran De Ferrer et al., "NR 06. Sugar Production From Rice Straw", Arch. Latinoam. Prod. Anim. 5(Supl. 1), 1997, pp. 112-114.
Topic 3 R&D on Processes for Solid, Liquid and Gaseous Fuels From Biomass, 20th EU BC&E.
Wilson, Jonathan, "A Cost Analysis for the Densification and Transportation of Cellulosic Biomass for Ethanol Production", Kansas State University, 2011, 86 pgs.
U.S. Appl. No. 12,226,763, Response Filed Dec. 21, 2011 to Office Action Mailed Aug. 22, 2011.
U.S. Appl. No. 12/226,763, Final Rejection Mailed on Jan. 10, 2012.
U.S. Appl. No. 12/226,763, Notice of Allowance Mailed on May 29, 2012.
U.S. Appl. No. 12/226,763, Notice of Allowance Mailed on Oct. 1, 2012.
U.S. Appl. No. 12/226,763, Notice of Allowance Mailed on Jan. 22, 2013.
U.S. Appl. No. 12,791,703, Response Filed Oct. 11, 2012 to Office Action Mailed Jul. 27, 2012.
U.S. Appl. No. 12/976,344, Notice of Allowance Mailed on Feb. 23, 2012.
U.S. Appl. No. 13/202,011, NonFinal Rejection Mailed on Sep. 27, 2012.
U.S. Appl. No. 13/202,011, Response file Dec. 21, 2012 to NonFinal Rejection Mailed on Sep. 27, 2012.
U.S. Appl. No. 13/591,092, Office Action Mailed on Dec. 13, 2012.
Australian Application No. 2010249409, Examination Report Mailed on Aug. 30, 2012.
Australian Application No. 2010289797, Examination Report Mailed on Oct. 30, 2012.
Australian Application No. 2011201768, Examination Report Mailed on Jun. 21, 2012.
Brazilian Application No. PI0722418-4, Office Action Jan. 14, 2013.
Canadian Application No. 2,650,860, Response Filed Apr. 23, 2012 to Office Action Mailed on Oct. 24, 2011.
Canadian Application No. 2,650,860, Office Action Mailed on Jun. 18, 2012.
Canadian Application No. 2,650,860, Response Filed Dec. 13, 2012 to Office Action Mailed on Jun. 18, 2012.

(56) References Cited

OTHER PUBLICATIONS

Canadian Application No. 2,737,704, Office Action Mailed on Jun. 4, 2012.
Canadian Application No. 2,737,704, Response Filed Aug. 22, 2012 to Office Action Mailed on Jun. 4, 2012.
Canadian Application No. 2,737,704, Office Action Mailed on Nov. 5, 2012.
Canadian Application No. 2,737,704, Response Filed Jan. 30, 2013 to Office Action Mailed on Nov. 5, 2012.
Canadian Application No. 2,737,704, Office Action Mailed on Feb. 21, 2013.
Canadian Application No. 2,760,840, Office Action Mailed on Mar. 28, 2012.
Canadian Application No. 2,760,840, Response Filed Jun. 27, 2012 to Office Action mailed on Mar. 28, 2012.
Canadian Application No. 2,760,840, Office Action Mailed on Aug. 6, 2012.
Canadian Application No. 2,760,840, Response Filed Nov. 6, 2012 to Office Action Mailed on Aug. 6, 2012.
Canadian Application No. 2,760,840, Office Action Mailed on Jan. 3, 2013.
Canadian Application No. 2,762,985, Office Action Mailed on Mar. 13, 2012.
Canadian Application No. 2,762,985, Response Filed Jun. 12, 2012 to Office Action Mailed on Mar. 13, 2012.
Canadian Application No. 2,762,985, Office Action Mailed on Jul. 6, 2012.
Canadian Application No. 2,762,985, Response Filed on Oct. 5, 2012 to Office Action Mailed on Jul. 6, 2012.
Canadian Application No. 2,762,985, Notice of Allowance Mailed on Oct. 29, 2012.
Chinese Application No. 200780025394.4, Office Action Mailed Oct. 30, 2012.
Chinese Application No. 200780025394.4, Response Filed Jan. 14, 2013 to Office Action Mailed Oct. 30, 2012.
Chinese Application No. 201110097994.X, Office Action Mailed on Jul. 30, 2012.
European Application No. 07776479.3, Office Action Mailed on May 30, 2012.
European Application No. 07776479.6, Response Filed Sep. 30, 2012 to Office Action Mailed on May 30, 2012.
European Application No. 07776479.3, Office Action Mailed on Dec. 5, 2012.
European Application No. 10814256.3, Search Report Mailed on Jan. 23, 2013.
European Application No. 11162906.9, Response Filed on Jul. 5, 2012 to Office Action Mailed on Jan. 16, 2012.
European Application No. 11772569.7, Office Action Mailed on Nov. 30, 2012.
International Application No. PCT/US2010/046525, International Preliminary Report on Patentability Mailed on Mar. 8, 2012.
International Application No. PCT/US2011/061617, International Search Report Mailed on Jun. 8, 2012.
International Application No. PCT/US2011/066868, International Search Report Mailed on Sep. 19, 2012.
International Application No. PCT/US2011/066868, Written Opinion Mailed on Sep. 19, 2012.
Mexican Application No. MX/a/2011/012357, Office Action.
Alizadeh, Hasan et al., "Pretreatment of Switchgrass by Ammonia Fiber Explosion (AFEX)", Applied Biochemistry and Biotechnology, vol. 121-124, 2005, 9 pgs.
Bergner, Hans., "Archives of Animal Nutrition", Arch. Tierernahr., vol. 30, 1980, 19 pgs.
Deshusses, Marc A., "Biological Waste Air Treatment in Biofilters", Current Opinion in Biotechnology, vol. 8, 1997, 335-339.
Kumar, Parveen et al., "Methods for Pretreatment of Lignocellulosic Biomass for Efficient Hydrolysis and Biofuel Production", Ind. Eng. Chem. Res., Mar. 20, 2009, 18 pgs.
Extended European Search Report received for European Patent Application No. 11162906.9, mailed on Dec. 13, 2011, 14 pages.

Notice of Allowance received for U.S. Appl. No. 12/976,344, mailed on Mar. 27, 2012, 8 pages.
Adapa et al., "Compression Characteristics of Selected Ground Agricultural Biomass", Agricultural Engineering International: the CIGR Ejournal, Manuscript 1347, vol. X!, Jun. 2009, 19 pages.
Allan et al., "Replacement of Fish Meal in Diets for Australian Silver Perch, Bidyanus Bidyanus: I. Digestibility of Alternative Ingredients", Aquaculture, vol. 186, No. 3-4, Jun. 2000, pp. 293-310.
Betschart et al., "Extractability and Solubility of Leaf Protein", J. Agr. Food Chem., vol. 21, No. 1, 1973, pp. 60-65.
El-Adawy et al., "Nutritional Potential and Functional Properties of Sweet and Bitter Lupin Seed Protein Isolates", Food Chemistry, vol. 74, No. 4, 2001, pp. 455-462.
Fernandez et al., "Protein Extraction from Atriplex Lampa Leaves: Potential Use as Forage for Animals used for Human Diets", Plant Foods for Human Nutrition, vol. 54, No. 3, 1999, pp. 251-259.
Ferrer et al., "Optimizing Ammonia Pressurization/Depressurization Processing Conditions to Enhance Enzymatic Susceptibility of Dwarf Elephant Grass", Applied Biochemistry and Biotechnology, vol. 84-86, No. 1-9, Mar. 2000, pp. 163-179.
Fiorentini et al., "Pilot Plant Production of an Edible Alfalfa Protein Concentrate", Journal of Food Science, vol. 46, No. 5, Sep. 1981, pp. 1514-1517.
Greene et al., "Growing Energy: How Biofuels Can Help End America's Oil Dependence", Natural Resources Defense Council, Dec. 2004, 86 pages.
Holtzapple et al., "The Ammonia Freeze Explosion (AFEX) Process: A Practical Lignocellulose Pretreatment", Applied Biochemistry and Biotechnology, vol. 28-29, No. 1, 1991, pp. 59-74.
Lau et al., "Comparing the Fermentation Performance of *Escherichia coli* KO11, *Saccharomyces cerevisiae* 424A (LNH-ST) and Zymomonas mobilis AX101 for Cellulosic Ethanol Production", Biotechnology for Biofuels, vol. 3, No. 11, 2010, 10 pages.
Lin et al., "Ethanol Fermentation from Biomass Resources: Current State and Prospects", Applied Microbiology and Biotechnology, vol. 69, No. 6, Feb. 2006, pp. 627-642.
Lovrien et al., "Assays for Total Protein", Current Protocols in Protein Science, 1995, pp. 3.4.1-3.4.24.
Madakadze et al., "Cutting Frequency and Nitrogen Fertilization Effects on Yield and Nitrogen Concentration of Switchgrass in a Short Season Area", Crop Science, vol. 39, No. 2, Mar.-Apr. 1999, pp. 552-557.
Ordonez et al., "Obtaining a Protein Concentrate from Integral Defatted Sunflower Flour", Bioresource Technology, vol. 78, No. 2, 2001, pp. 187-190.
Park et al., "Investigation and Optimization of the Factors Influencing Sorghum Protein Extraction", Journal of Agricultural and Food Chemistry, vol. 51, No. 24, Oct. 2003, pp. 7050-7054.
Rosa et al., "Integrated Production of Ethanol Fuel and Protein From Coastal Bermudagrass", Applied Biochemistry and Biotechnology, vol. 45-46, No. 1, 1994, pp. 483-497.
Sanderson et al., "Switchgrass as a Sustainable Bioenergy Crop", Bioresource Technology, vol. 56, No. 1, Apr. 1996, pp. 83-93.
Sluiter et al., "Determination of Structural Carbohydrates and Lignin in Biomass", National Renewable Energy Laboratory, Laboratory Analytical Procedure (LAP), Technical Report, NREL/TP-510-42618, Apr. 25, 2008, 17 pages.
Sukumaran et al., "Cellulase Production Using Biomass Feed Stock and Its Application in Lignocellulose Saccharification for Bio-Ethanol Production", Renewable Energy, vol. 34, No. 2, Feb. 2009, pp. 421-424.
Sulbaran-De-Ferrer et al., "Enzymatic Hydrolysis of Ammonia-Treated Rice Straw", Applied Biochemistry and Biotechnology, vol. 105-108, 2003, pp. 155-164.
Suto et al., "Induction and Catabolite Repression Mechanisms of Cellulase in Fungi", Journal of Bioscience and Bioengineering, vol. 92, No. 4, 2011, pp. 305-311.
Urribarri et al., "Leaf Protein from Ammonia-Treated Dwarf Elephant Grass (*Pennisetum purpureum* Schum cv. Mott)", Applied Biochemistry and Biotechnology, vol. 121-124, 2005, pp. 721-730.
Zhou et al., "Gene Integration and Expression and Extracellular Secretion of Erwinia chrysanthemi Endoglucanase CelY (celY) and

(56) References Cited

OTHER PUBLICATIONS

CelZ (celZ) in Ethanologenic Klebsiella oxytoca P2", Applied and Environmental Microbiology, vol. 67, No. 1, Jan. 2001, pp. 6-14.
Zhu et al., "Cocurrent Downflow Circulating Fluidized Bed (Downer) Reactors—A State of the Art Review", The Canadian Journal of Chemical Engineering, vol. 73, Oct. 1995, pp. 662-677.
Jin et al., "Two-Step SSCF to Convert AFEX-Treated Switchgrass to Ethanol using Commercial Enzymes and *Saccharomyces cerevisiae* 424A (LNH-ST)", Bioresource Technology, vol. 101, No. 21, 2010, pp. 8171-8178.
Kim et al., "Lime Pretreatment and Enzymatic Hydrolysis of Corn Stover", Bioresource Technology, vol. 96, No. 18, Dec. 2005, pp. 1994-2006.
Kim et al., "Pretreatment and Fractionation of Corn Stover by Ammonia Recycle Percolation Process", Bioresource Technology, vol. 96, No. 18, 2005, pp. 2007-2013.
Kim et al., "Pretreatment of Corn Stover by Low-Liquid Ammonia Recycle Percolation Process", Applied Biochemistry and Biotechnolology, vol. 133, Apr. 2006, pp. 41-57.
Kumar et al., "Does Densification Influence the Steam Pretreatment and Enzymatic Hydrolysis of Softwoods to Sugars?", Bioresource Technology, vol. 121, Oct. 2012, pp. 190-198.
Ladisch et al., "Buiding a Bridge to the Ethanol Industry—Follow-Up Project", National Renewable Energy Laboratory, Apr. 2003, 36 pages.
Lau et al, "Cellulosic Ethanol Production from AFEX-treated Corn Stover Using *Saccharomyces cerevisiae* 424A(LNH-ST)", PNAS, vol. 106, No. 5, Feb. 3, 2009, pp. 1368-1373.
Lau et al., "Ethanol Fermentation of *E. coli* KO11 in Hydrolysate from AFEX-treated Corn Stover", Biomass Conversion Research Laboratory, Department of Chemical Engineering and Materials Science, Prior to May 2, 2013, 1 page.
Lau et al., "The Impacts of Pretreatment on the Fermentability of Pretreated Lignocellulosic Biomass: A Comparative Evaluation between Ammonia Fiber Expansion and Dilute Acid Pretreatment", Biotechnology for Biofuels, vol. 2, No. 30, 2009, 11 pages.
Laureano-Perez et al., "Understanding Factors That Limit Enzymatic Hydrolysis of Biomass—Characterization of Pretreated Corn Stover", Applied Biochemistly and Biotechnology, vol. 121-124, 2005, pp. 1081-1099.
Liu et al., "Partial Flow of Compressed-Hot Water through Corn Stover to Enhance Hemicellulose Sugar Recovery and Enzymatic Digestibility of Cellulose", Bioresource Technology, vol. 96, No. 18, 2005, pp. 1978-1985.
Lloyd et al., "Combined Sugar Yields for Dilute Sulfuric Acid Pretreatment of Corn Stover Followed by Enzymatic Hydrolysis of the Remaining Solids", Bioresource Technology, vol. 96, vol. 18, Dec. 2005, pp. 1967-1977.
Lu et al., "Celulase Adsorption and an Evaluation of Enzyme Recycle During Hydrolysis of Steam-Exploded Softwood Residues", Applied Biochemistry and Biotechnology, vol. 98-100, 2002, pp. 641-654.
Mani et al., "Economics of Producing Fuel Pellets from Biomass", Applied Engineering in Agriculture, vol. 22, No. 3, pp. 421-426, Jan. 1, 2006.
Marshall et al., "Complete Rations for Dairy Cattle. II. Sugarcane Bagasse Pellets as Roughage in Blended Rations for Lactating Cows", Journal of Dairy Science, vol. 58, No. 6, Jun. 1975, pp. 896-900.
Mosier et al., "Optimization of pH Controlled Liquid Hot Water Pretreatment of Corn Stover", Bioresource Technology, vol. 96, 2005, pp. 1986-1993.
Paul et al., "Liquid-Vapor Interfacial Properties of Water-Ammonia Mixtures: Dependence on Ammonia Concentration", The Journal of Chemical Physics, vol. 123, No. 17, 2005, 10 pages.
Perry et al., "Reaction Kinetics and Reactor Design", Chemical Engineers' Handbook, Fourth Edition, 1963, pp. 4-21-4-24.
Piva et al., "Detoxification Methods of Aflatoxins. A Review", Nutrition Research, vol. 15, No. 5, May 1995, pp. 767-776.

Prévot-D'Alvise et al., "Development of a Pilot Process for the Production of Alfalfa Peptide Isolate", Journal of Chemical Technology and Biotechnology, vol. 78, Issue 5, May 2003, pp. 518-528.
Rijal et al., "Combined Effect of Pelleting and Pretreatment on Enzymatic Hydrolysis of Switchgrass", Bioresource Technology, vol. 116, 2012, pp. 36-41.
Rollin et al., "Increasing Cellulose Accessibility is More Important Than Removing Lignin: A Comparison of Cellulose Solvent-Based Lignocellulose Fractionation and Soaking in Aqueous Ammonia", Biotechnology and Bioengineering, vol. 108, No. 1, Jan. 1, 2011, pp. 22-30.
Roman-Ponce et al., "Complete Rations for Dairy Cattie. V. Interaction of Sugarcane Bagasse Quantity and Form with Soybean Meal, Urea, and Starea", Journal of Dairy Science, vol. 58, No. 9, Sep. 1975, pp. 1320-1327.
Selig et al., "Enzymatic Saccharification of Lignocellulosic Biomass", National Renewable Energy Laboratory, Report, NREL/TP-510-42629, Mar. 21, 2008, 8 pages.
Sendich et al., "Recent Process Improvements for the Ammonia Fiber Expansion (AFEX) Process and Resulting Reductions in Minimum Ethanol Selling Price", Bioresource Technology, vol. 99, 2008, pp. 8429-8435.
Sokhansanj et al., "Biomass Densification—Cubing Operation and Costs for Corn Stover", Applied Engineering in Agriculture, vol. 20, No. 4, American Society of Agricultural Engineers, 2004, pp. 495-499.
Somerville et al., "Toward a Systems Approach to Understanding Plant Cell Walls", Science, vol. 306, No. 570524 Dec. 24, 2004, pp. 2206-2211.
Steele et al., "Enzyme Recovery and Recycling Following Hydrolysis of Ammonia Fiber Explosion—Treated Corn Stover", Applied Biochemisty and Biotechnology, vol. 121-124, No. 1-3, 2005, pp. 901-910.
SunOpta BioProcess Group, "SunOpta BioProcess Solutions", Customer Manual, Prior to Apr. 19, 2010, 20 pages.
Tabil et al., "Biomass Feedstock Pre-Processing—Part 1: Pre-Treatment", Chapter 18, Biofuel's Engineering Process Technology, Aug. 2011, pp. 411-438.
Tanner Industries, Inc., "Anhydrous Ammonia", Customer Manual, Dec. 2006, 17 pages.
Teymouri et al., "Hydrolysis of Ground and Unground AFEX Treated Corn Stover with Different Combinations of Cellulase and Xylanase", 27th Symposium on Biotechnology for Fuels and Chemicals, May 1-4, 2005, 21 pages.
Theerarattananoon et al., "Effects of the Pelleting Conditions on Chemical Composition and Sugar Yield of Corn Stover, Big Bluestem, Wheat Straw, and Sorghum Stalk Pellets", Bioprocess Biosyst. Eng., vol. 35, No. 4, May 2012, pp. 615-623.
Tolan Jeffrey S., "Iogen's Demonstration Process for Producing Ethanol from Cellulosic Biomass", Fuel-oriented Biorefineries, Chapter 9, Biorefineries—Industrial Processes and Products, 2006, pp. 193-208.
Van Horn et al., "Complete Rations for Growing Dairy Replacements Utilizing By-Product Feed stuffs", Journal of Science, vol. 63, 1980, pp. 1465-1474.
Walter, A., "Industrial Uses of Biomass Energy: New Technologies for Modern Biomass Energy Carriers", Taylor & Francis, Chapter 9, edited by Rosillo-Calle F., Bajay SV, Rothman H., 2000, pp. 200-253.
Wang et al., "Cost Estimates and Sensitivity Analyses for the Ammonia Fiber Explosion Process", Applied Biochemistry and Biotechnology, vol. 70-72, No. 1, 1998, pp. 51-66.
Zhang et al., "The Effect of Different Treatment Conditions on Biomass Binder Preparation for Lignite Briquette", Fuel Processing Technology, vol. 73, 2001, pp. 185-196.
Zhong et al., "Optimization of Enzymatic Hydrolysis and Ethanol Fermentation from AFEX-Treated Rice Straw", Applied Microbiology and Biotechnology, vol. 84, No. 4, Springer-Verlag, Sep. 2009, pp. 667-676.
Office Action received for European Patent Application No. 10814256.3, mailed on Sep. 6, 2013, 4 pages.
Non-Final Office Action received for U.S. Appl. No. 11/719,158, mailed on Apr. 1, 2009, 6 pages.

(56) References Cited

OTHER PUBLICATIONS

Final Office Action received for U.S. Appl. No. 11/719,158, mailed on Aug. 4, 2010, 7 pages.
Notice of Allowance received for U.S. Appl. No. 11/719,158, mailed on Jan. 6, 2011, 4 pages.
Office Action received for European Patent Application No. 11162906.9, mailed on Mar. 6, 2013, 5 pages.
Extended European Search Report for European Patent Application No. 11850707.8, mailed on Jul. 3, 2014, 8 pages.
Non Final Office Action received for U.S. Appl. No. 12/286,913, mailed on Sep. 28, 2011, 7 pages.
Notice of Allowance received for U.S. Appl. No. 12/286,913, mailed on Oct. 3, 2012, 9 pages.
Advisory Action received for U.S. Appl. No. 12/763,102, mailed on Dec. 6, 2013, 3 pages.
Final Office Action received for U.S. Appl. No. 12/763,102, mailed on Aug. 5, 2013, 12 pages.
Non Final Office Action received for U.S. Appl. No. 12/763,102, mailed on Dec. 24, 2012, 18 pages.
Restriction Requirement received for U.S. Appl. No. 12/763,102, mailed on Sep. 17, 2012, 11 pages.
Non-Final Office Action received for U.S. Appl. No. 12/791,703, mailed on Jul. 27, 2012, 7 pages.
Notice of Allowance received for U.S. Appl. No. 12/791,703, mailed on Nov. 8, 2012, 8 pages.
Non-Final Office Action received for U.S. Appl. No. 12/976,344, mailed on Apr. 5, 2013, 12 pages.
Non-Final Office Action received for U.S. Appl. No. 12/976,344, mailed on Apr. 1, 2014, 19 pages.
Restriction Requirement received for U.S. Appl. No. 13/202,011, mailed on Jul. 17, 2012, 6 pages.
Notice of Allowance received for U.S. Appl. No. 13/202,011, mailed on Apr. 9, 2013, 9 pages.
Notice of Allowance received for U.S. Appl. No. 13/202,011, mailed on Nov. 8, 2013, 7 pages.
Notice of Allowance received for U.S. Appl. No. 13/458,830, mailed on Jul. 9, 2014, 8 pages.
Advisory Action received for U.S. Appl. No. 13/591,092, mailed on Jun. 6, 2013, 3 pages.
Final Office Action received for U.S. Appl. No. 13/591,092, mailed on Mar. 25, 2013, 22 pages.
Notice of Allowance received for U.S. Appl. No. 13/591,092, mailed on Feb. 21, 2014, 11 pages.
Office Action received for Canadian Patent Application No. 2,760,840, mailed on Jan. 3, 2013, 3 pages.
Office Action received for Canadian Patent Application No. 2,760,840, mailed on Jul. 30, 2013, 4 pages.
Office Action received for Chinese Patent Application No. 201110097994.X, mailed on Mar. 27, 2013, 7 pages (English Translation).
Examination Report received for Australian Patent Application No. 2011348161, mailed on Feb. 21, 2014, 4 pages.
Office Action received for Chinese Patent Application No. 201210287568.7, mailed on Jul. 26, 2013, 3 pages English Translation.
Examination Report received for Australian Patent Application No. 2013205681, mailed on Jun. 27, 2013, 4 pages.
Notice of Allowance received for Canadian Patent Application No. 2,650,860, mailed on Apr. 2, 2013, 1 page.
International Search Report and Written Opinion received for PCT Patent Application No. PCT/US2011/038524, mailed on Feb. 9, 2012, 7 pages.
International Preliminary Report on Patentability received for PCT Patent Application No. PCT/US2011/066868, mailed on Jul. 4, 2013, 5 pages.
International Search Report and Written Opinion received for PCT Patent Application No. PCT/US2012/059898, mailed on Jul. 26, 2013, 11 pages.
International Search Report and Written Opinion received for PCT Patent Application No. PCT/US2013/028689, mailed on Jun. 4, 2013, 5 pages.
International Search Report received for PCT Patent Application No. PCT/US2013/037935, mailed on Jul. 19, 2013, 4 pages.
Adapa et al., "Pelleting Characteristics of Selected Biomass With and Without Steam Explosion Pretreatment", International Journal of Agricultural and Biological Engineering, vol. 3, No. 3, Sep. 2010, pp. 62-79.
Balan et al., "Lignocellulosic Biomass Pretreatment Using AFEX", Biofuels: Methods and Protocols, Methods in Biology, Chapter 5, vol. 581, 2009, pp. 61-77.
Bals et al., "Enzymatic Hydrolysis of Distiller's Dry Grain and Solubles (DDGS) Using Ammonia Fiber Expansion Pretreatment", Energy & Fuels 2006, vol. 20, No. 6, American Chemical Society, Oct. 2006, pp. 2732-2736.
Bals et al., "Evaluating the Impact of Ammonia Fiber Expansion (AFEX) Pretreatment Conditions on the Cost of Ethanol Production", Bioresource Technology, vol. 102, 2011, pp. 1277-1283.
Carolan et al., "Technical and Financial Feasibility Analysis of Distributed Bioprocessing Using Regional Biomass Pre-Processing Centers", Journal of Agricultural & Food Industrial Organization, vol. 5, No. 2, Article 10, Explorations in Biofuels Economics, Policy, and History, 2007, 29 pages.
Chundawat et al., "Multi-scale Visualization and Characterization of Lignocellulosic Plant Cell Wall Deconstruction During Thermochemical Pretreatment", Energy & Environmental Science, 2011, No. 4, The Royal Society of Chemistry, 2011, pp. 973-984.
Cosgrove, Daniel J., "Growth of the Plant Cell Wall", Nature Reviews Molecular Cell Biology 6, Nov. 2005, pp. 850-861.
Dale et al., "Extrusion Processing for Ammonia Fiber Explosion (AFEX)", Applied Biochemistry and Biotechnology, vol. 77-79, 1999, pp. 35-45.
Dale et al., "Fermentation of Lignocellulosic Materials Treated by Ammonia Freeze-Explosion", Developments in Industrial Microbiology, vol. 26, The Society for Industrial Microbiology, 1985, pp. 223-233.
Eggeman, T., "Boundary Analysis for H2 Production by Fermentation", NREL National Renewal Energy Laboratory, Subcontract Report NREL/SR-560-36129, May 2005, 17 pages.
Erickson, David R., "Edible Fats and Oils Processing: Basic Principles and Modern Practices", AOCS Press, Netherlands, 1990, 6 pages.
Gao et al., "Mixture Optimization of Six Core Glycosyl Hydrolases for Maximizing Saccharification of Ammonia Fiber Expansion (AFEX) Pretreated Corn Stover", Bioresource Technology, vol. 101, Issue 8, Apr. 2010, pp. 2770-2781.
Hanchar et al., "Separation of Glucose and Pentose Sugars by Selective Enzyme Hydrolysis of AFEX-Treated Corn Fiber", Applied Biochemistry and Biotechnology, vol. 137-140, No. 1-12, 2007, pp. 313-326.
Jin et al., "A Novel Integrated Biological Process for Cellulosic Ethanol Production Featuring Hich Ethanol Productivity, Enzyme Recycling and Yeast Cells Reuse", Energy & Environmental Science, No. 5, 8 pages, Nov. 2, 2011.

\* cited by examiner

Protein Content of AFEX-Corn Stover Hydrolysate at 18% Solids Loading

|     | Total Protein | Free AA |
|-----|---------------|---------|
|     | mg/L          |         |
| NH₃ | 800±50        |         |
| Asp | 75.9±1.7      | 8.4±1.1 |
| Glu | 133.8±2.4 | 0.0±0.0 |
| Ser | 104.2±3.8     | 16.8±1.7 |
| Gly | 127.2±5.8     | 5.2±0.7 |
| His | 34.3±2.3      | 4.5±0.5 |
| Thr | 98.9±4.6      | 17.6±0.6 |
| Arg | 55.0±3.2      | 17.1±2.1 |
| Ala | 110.2±2.9     | 11.6±2.0 |
| Pro | 108.7±2.3     | 30.4±6.4 |
| Tyr | 28.6±2.5      | 30.0±5.8 |
| Val | 68.8±2.2      | 9.9±2.2 |
| Met | 19.4±1.9 | 2.6±1.2 |
| Ile | 55.4±2.2      | 7.6±0.9 |
| Leu | 93.6±3.8      | 0.0±0.0 |
| Lys | 25.7±1.3      | 18.4±2.3 |
| Phe | 91.6±3.8      | 15.7±1.3 |
| Total | 1231.2±43.9 | 195.8±28.3 |

FIGURE 12

**Trace Element and Vitamin Content
of AFEX-Corn Stover Hydrolysate at 18% Solids Loading**

| | | Unit | AFEX-Hydrolysate | Reference Value (Walker, 2004) |
|---|---|---|---|---|
| Trace Elements | K | mg/L | 170.44±0.66 | 76 |
| | Mg | | 26.63±0.83 | 48 |
| | Ca | | 45.62±1.27 | 0.02 |
| | Mn | | 0.19±0.00 | 0.1 |
| | Co | | 0.01±0.00 | 0.0027 |
| | Ni | | 0.08±0.00 | 0.28 |
| | Cu | | 0.09±0.00 | 0.0435 |
| | Zn | | 0.19±0.01 | 0.24 |
| | Mo | | 0.05±0.00 | 0.063 |
| | Fe | | 0.32±0.01 | 0.078 |
| Vitamins | | μM | 3.01±0.08 | 0.68-1.14 |
| | | | 2.14±0.00 | 0.89-1.18 |
| | | | 26.78±0.22 | 12.18-20.31 |
| | | | ~0.10 | 0.02-0.04 |
| | | | ~0.40 | 0.57-2.83 |

FIGURE 13

Main Conclusions

- AFEX-CS oligomers are 2.5-7 times more potent than lactose (compared on the same weight basis)
- Total soluble sugar yield was comparable to that of standard enzyme mixture (Acellerase Multifect Pectinase and Multifect Xylanase) at 10 mg/g CS
- To archive similar moneric sugar yield, 1.5 mg/g CS of Accellerase is needed
- The enzyme concentration of the Trichoderma broth is sufficient to support effective sugar solubilization at 6.0% glucan loading (~18% solids loading)

FIGURE 16

Main Conclusions:

- Native S, cerevisiae cells (Non-Genetically-Modified) were produced as a coproduct for the biorefinery.
- Recombinant S, cerevisiae can be recycled at least for 4 cycles without the need for new cells. This facilitates cost-effective fermentation high cell density.
- Ethanol at 40 g/L was achieved in the end of the fermentations

EXTRACTION OF SOLUBLES FROM PLANT BIOMASS FOR USE AS MICROBIAL GROWTH STIMULANT AND METHODS RELATED THERETO

This application is a continuation-in-part of U.S. patent application Ser. No. 11/897,119 filed Aug. 29, 2007 now abandoned, which is incorporated by reference herein its entirety. This application is also a continuation-in-part of U.S. patent application Ser. No. 12/226,850 filed Jun. 22, 2009 now abandoned, which is a U.S. National Stage filing under 35 U.S.C. 371 from International Application No. PCT/US2007/010410 filed Apr. 30, 2007 and published in English as WO 2008/020901 on Feb. 21, 2008 (hereinafter "'020901"), which claims priority under 35 U.S.C. 119(e) to U.S. Provisional Patent Application Ser. No. 60/796,401 filed May 1, 2006, which applications and publications are hereby incorporated herein by reference in their entireties.

STATEMENT OF GOVERNMENT RIGHTS

This invention was made with government support under DE-FC02-07ER64494 and DE-FG36-04GO14220 awarded by the U.S. Department of Energy. The government has certain rights in the invention.

BACKGROUND

Cellulosic biomass can be used for the production of various products. However, many conventional methods are very expensive, requiring high capital expenditures, such as for high pressure reactors and large amounts of additives.

BRIEF DESCRIPTION OF THE DRAWINGS

FIG. 12 shows a chart of total protein and free AA for various constituents in embodiments of the present invention.

FIG. 13 shows trace element and vitamin content of AFEX-corn stover hydrolysate at 18% solids loading in an embodiment of the present invention.

FIG. 16 provides relevant conclusions pertinent to one or more of FIGS. 11A, 11B, 12, 13, 14A, 14B and 15 in embodiment of the present invention.

DETAILED DESCRIPTION OF THE EMBODIMENTS

Figure 1:
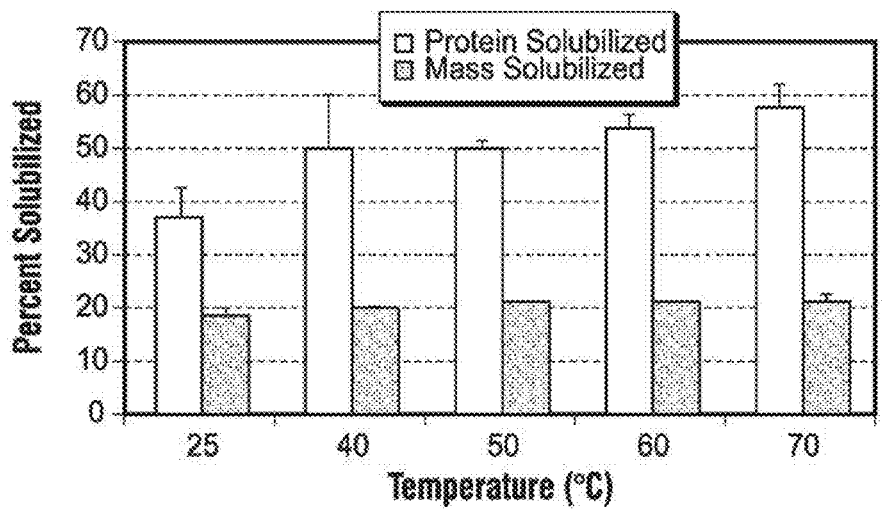
FIG. 1 is a graph showing the effect of extraction temperature on protein yields in embodiments of the present invention. All extractions were done with 3% ammonium hydroxide at pH=10.5 after an AFEX™ (hereinafter "AFEX") treatment. The results were combined after two (2) separate extractions using 11:1 liquid/solid ratio and 3 minute residence time. All runs were done in duplicate and error bars represent the maximum and minimum values.

In the following detailed description of the preferred embodiments, reference is made to the accompanying drawings, which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that chemical, procedural and other changes may be made without departing from the spirit and scope of the present invention. The following detailed description is, therefore, not to be taken in a limiting sense, and the scope of the present invention is defined only by the appended claims, along with the full scope of equivalents to which such claims are entitled.

The Detailed Description that follows begins with a definition section followed by a brief overview of current technologies for production of commercial products from cellulosic-based biomass, a description of the embodiments, an example section and a brief conclusion.

The term "biomass" as used herein, refers in general to organic matter harvested or collected from a renewable biological resource as a source of energy. The renewable biological resource can include plant materials, animal materials, and/or materials produced biologically. The term "biomass" is not considered to include fossil fuels, which are not renewable.

The term "plant biomass" or "ligno-cellulosic biomass" as used herein, is intended to refer to virtually any plant-derived organic matter (woody or non-woody) available for energy on a sustainable basis. Plant biomass can include, but is not limited to, agricultural crop wastes and residues such as corn stover, wheat straw, rice straw, sugar cane bagasse and the like. Plant biomass further includes, but is not limited to, woody energy crops, wood wastes and residues such as trees, including fruit trees, such as fruit-bearing trees, (e.g., apple trees, orange trees, and the like), softwood forest thinnings, barky wastes, sawdust, paper and pulp industry waste streams, wood fiber, and the like. Additionally grass crops, such as various prairie grasses, including prairie cord grass, switchgrass, big bluestem, little bluestem, side oats grama, and the like, have potential to be produced large-scale as additional plant biomass sources. For urban areas, potential plant biomass feedstock includes yard waste (e.g., grass clippings, leaves, tree clippings, brush, etc.) and vegetable processing waste. Plant biomass is known to be the most prevalent form of carbohydrate available in nature and corn stover is currently the largest source of readily available plant biomass in the United States.

The term "biofuel" as used herein, refers to any renewable solid, liquid or gaseous fuel produced biologically, for example, those derived from biomass. Most biofuels are originally derived from biological processes such as the photosynthesis process and can therefore be considered a solar or chemical energy source. Other biofuels, such as natural polymers (e.g., chitin or certain sources of microbial cellulose), are not synthesized during photosynthesis, but can nonetheless be considered a biofuel because they are biodegradable. There are generally considered to be three types of biofuels derived from biomass synthesized during photosynthesis, namely, agricultural biofuels (defined below), municipal waste biofuels (residential and light commercial garbage or refuse, with most of the recyclable materials such as glass and metal removed) and forestry biofuels (e.g., trees, waste or byproduct streams from wood products, wood fiber, pulp and paper industries). Biofuels produced from biomass not synthesized during photosynthesis include, but are not limited to, those derived from chitin, which is a chemically modified form of cellulose known as an N-acetyl glucosamine polymer. Chitin is a significant component of the waste produced by the aquaculture industry because it comprises the shells of seafood.

The term "agricultural biofuel", as used herein, refers to a biofuel derived from agricultural crops (e.g., grains, such as corn), crop residues, grain processing facility wastes (e.g., wheat/oat hulls, corn/bean fines, out-of-specification materials, etc.), livestock production facility waste (e.g., manure, carcasses, etc.), livestock processing facility waste (e.g., undesirable parts, cleansing streams, contaminated materials, etc.), food processing facility waste (e.g., separated waste streams such as grease, fat, stems, shells, intermediate process residue, rinse/cleansing streams, etc.), value-added agricultural facility byproducts (e.g., distiller's wet grain (DWG) and syrup from ethanol production facilities, etc.), and the like. Examples of livestock industries include, but are not limited to, beef, pork, turkey, chicken, egg and dairy facilities. Examples of agricultural crops include, but are not limited to, any type of non-woody plant (e.g., cotton), grains such as corn, wheat, soybeans, sorghum, barley, oats, rye, and the like, herbs (e.g., peanuts), short rotation herbaceous crops such as switchgrass, alfalfa, and so forth.

The term "pretreatment step" as used herein, refers to any step intended to alter native biomass so it can be more efficiently and economically converted to reactive intermediate chemical compounds such as sugars, organic acids, etc., which can then be further processed to a variety of value added products such a value-added chemical, such as ethanol. Pretreatment can reduce the degree of crystallinity of a polymeric substrate, reduce the interference of lignin with biomass conversion and prehydrolyze some of the structural carbohydrates, thus increasing their enzymatic digestibility and accelerating the degradation of biomass to useful products. Pretreatment methods can utilize acids of varying concentrations (including sulfuric acids, hydrochloric acids, organic acids, etc.) and/or other components such as ammonia, ammonium, lime, and the like. Pretreatment methods can additionally or alternatively utilize hydrothermal treatments including water, heat, steam or pressurized steam. Pretreatment can occur or be deployed in various types of containers, reactors, pipes, flow through cells and the like. Most pretreatment methods will cause the partial or full solubilization and/or destabilization of lignin and/or hydrolysis of hemicellulose to pentose sugars.

The term "moisture content" as used herein, refers to percent moisture of biomass. The moisture content is calculated as grams of water per gram of wet biomass (biomass dry matter plus water) times 100%.

The term "Ammonia Fiber Explosion" or "Ammonia Fiber Expansion" (hereinafter "AFEX") pretreatment" as used herein, refers to a process for pretreating biomass with ammonia to solubilize lignin and redeposit it from in between plant cell walls to the surface of the biomass. An AFEX pretreatment disrupts the lignocellulosic matrix, thus modifying the structure of lignin, partially hydrolyzing hemicellulose, and increasing the accessibility of cellulose and the remaining hemicellulose to subsequent enzymatic degradation. Lignin is the primary impediment to enzymatic hydrolysis of native biomass, and removal or transformation of lignin is a suspected mechanism of several of the leading pretreatment technologies, including AFEX. However in contrast to many other pretreatments, the lower temperatures and non-acidic conditions of the AFEX process prevents lignin from being converted into furfural, hydroxymethyl furfural, and organic acids that could negatively affect microbial activity. The process further expands and swells cellulose fibers and further breaks up amorphous hemicellulose in lignocellulosic biomass. These structural changes open up the plant cell wall structure enabling more efficient and complete conversion of lignocellulosic biomass to value-added products while preserving the nutrient value and composition of the material. See, for example, the methods described in U.S. Pat. Nos. 6,106,888, 7,187,176, 5,037,663, and 4,600,590, all of which are hereby incorporated by reference in their entirety as if fully set forth herein.

Nearly all forms of lignocellulosic biomass, i.e., plant biomass, such as monocots, comprise three primary chemical fractions: hemicellulose, cellulose, and lignin. Hemicellulose is a polymer of short, highly-branched chains of mostly five-carbon pentose sugars (xylose and arabinose), and to a lesser extent six-carbon hexose sugars (galactose, glucose and mannose). Dicots, on the other hand, have a high content of pectate and/or pectin, which is a polymer of alpha-linked glucuronic acid. Pectate may be "decorated" with mannose or rhamnose sugars, also). These sugars are highly substituted with acetic acid.

Because of its branched structure, hemicellulose is amorphous and relatively easy to hydrolyze (breakdown or cleave) to its individual constituent sugars by enzyme or dilute acid treatment. Cellulose is a linear polymer of glucose sugars, much like starch, which is the primary substrate of corn grain in dry grain and wet mill ethanol plants. However, unlike starch, the glucose sugars of cellulose are strung together by β-glycosidic linkages which allow cellulose to form closely-associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers. Lignin, which is a polymer of phenolic molecules, provides structural integrity to plants, and remains as residual material after the sugars in plant biomass have been fermented to ethanol. Lignin is a by-product of alcohol production and is considered a premium quality solid fuel because of its zero sulfur content and heating value, which is near that of sub-bituminous coal.

Typically, cellulose makes up 30 to 50% of residues from agricultural, municipal, and forestry sources. Cellulose is more difficult to hydrolyze than hemicellulose, but, once hydrolyzed, converts more efficiently into ethanol with glucose fermentation than hemicellulose. In contrast, the sugar polymers of hemicellulose are relatively easy to hydrolyze, but do not convert as efficiently as cellulose using standard fermentation strains (which produce ethanol from glucose). Although hemicellulose sugars represent the "low-hanging" fruit for conversion to ethanol, the substantially higher content of cellulose represents the greater potential for maximizing alcohol yields, such as ethanol, on a per ton basis of plant biomass.

Conventional methods used to convert biomass to alcohol include processes employing a concentrated acid hydrolysis pretreatment, a two-stage acid hydrolysis pretreatment as well as processes employing any known conventional pretreatment, such as hydrothermal or chemical pretreatments, followed by an enzymatic hydrolysis (i.e., enzyme-catalyzed hydrolysis) or simultaneous enzymatic hydrolysis and saccharification. Such pretreatment methods can include, but are not limited to, dilute acid hydrolysis, high pressure hot water-based methods, i.e., hydrothermal treatments such as steam explosion and aqueous hot water extraction, reactor systems (e.g., batch, continuous flow, counter-flow, flow-through, and the like), AFEX, ammonia recycled percolation (ARP), lime treatment and a pH-based treatment. However, pretreatment-hydrolysis of plant biomass can often result in the creation and release of other chemicals that inhibit microbial fermentation. These inhibitors (i.e. furfural) are largely the product of sugar degradation, and methods to remove these inhibitors or to reduce their formation or strains resistant to the inhibitors are needed.

Several of these methods generate nearly complete hydrolysis of the hemicellulose fraction to efficiently recover high yields of the soluble pentose sugars. However, chemical solubilization of hemicellulose also produces toxic products, such as furan derivatives, which can inhibit downstream microbial reactions (e.g., fermentation). Regardless, the hydrolysis of hemicellulose facilitates the physical removal of the surrounding hemicellulose and lignin, thus exposing the cellulose to later processing. However, most, if not all, pretreatment approaches do not significantly hydrolyze the cellulose fraction of biomass.

Biomass conversion to alcohol also poses unique fermentation considerations. The *Saccharomyces cerevisiae* yeast strains used in conventional corn ethanol plants for example, can ferment glucose, but cannot ferment pentose sugars such as xylose. Additionally, there is currently no naturally occurring microorganism that can effectively convert all the major sugars present in plant biomass to ethanol. Therefore, genetically engineered yeast or bacteria, which can, in theory, ferment both glucose and xylose to alcohol, are being used for biomass to alcohol processes. However, in practice, co-fermentation is inefficient and glucose fermentation is still the main reaction for ethanol production. Furthermore, genetically-enhanced recombinant strains of fermentative microorganisms, including recombinant strains of yeast, bacteria and fungi, as well as transgenic nucleic acids (DNA, RNA) derived from such component may pose environmental disposal and permitting problems.

Growing concerns about the environmental, political, and economic impact of oil use have spurred renewed interest in alternative fuels for transportation. Ethanol derived from cellulosic feedstocks such as agricultural waste, wood chips, municipal waste, or forages is one particularly attractive alternative because it is domestically available, renewable, and can potentially reduce greenhouse gas emissions (1).

Switch grass (*Panicum vergatum*) is a model herbaceous energy crop, and is attractive as a feedstock due to several favorable characteristics: high crop yields, low soil erosion, low water, fertilizer and pesticide requirements, ability to sequester carbon, and high genetic variability (2-3). In order to ferment the carbohydrates in cellulosic feedstocks into ethanol, they must first be broken down into their component sugars. However, yields from enzymatic hydrolysis are low unless the biomass first undergoes a pretreatment process, such as the AFEX process described herein.

Although the structural carbohydrates in lignocellulosic feedstocks are the largest component in plant biomass, several other components are present as well, which can provided added value. In particular, proteins are a potentially valuable co-product which can be separated from the rest of the biomass and sold as animal feed or other value added products. Such a process could have numerous benefits, including potentially decreasing the cost of producing ethanol. Greene et al. estimate that extracting proteins from switch grass in a mature biorefinery could reduce the selling price of ethanol by nearly 20%. Furthermore, an acre of switch grass can produce at least as much protein as an acre of soybean, providing the opportunity to replace soy acreage with switch grass, and thereby increasing the total amount of biofuels able to be produced in the United States without reducing the capacity to produce animal feed.

Industrial microbial processes ("fermentations") require a mixture of nutrients to support microbial growth and product formation. These nutrient mixtures are generally termed "Microbial Growth Stimulants" (MGS). Corn Steep Liquor (CSL) from corn milling processes is one such microbial growth stimulant. The expected significant increase in fermentation processes to produce fuels and chemicals from plant matter will require a similar increase in volume of growth stimulants used.

Microbial growth supplements such as Corn Steep Liquor (CSL) produced from corn kernel (grain) processing byproducts are well known and have proven very valuable in increasing the rate and yield of fermentation products, including pharmaceutical products such as penicillin and fuels such as ethanol. However, such supplements are relatively costly and will likely become even more costly in the future.

The inventors recognize the need for improved and more economical Microbial Growth Stimulants (MGSs) derived from herbaceous biomass rather than from Corn Steep Liquor (CSL). These novel MGSs described herein can compete in all types of fermentation industries, as well as in animal feed rations. In one embodiment, a process for producing a Microbial Growth Stimulant (MGS) solution from an Ammonia Fiber Expansion (AFEX) process pretreated plant biomass is provided. The process uses a relatively dilute ammonium hydroxide solution to extract the proteins from the plant biomass which after removal of at least some of the proteins becomes the microbial growth stimulant solution. In one embodiment, the process is part of a process for extracting and hydrolyzing extracted sugar precursors (carbohydrates) from the plant biomass which are hydrolyzed into sugars which are used in a fermentation to produce ethanol.

In one embodiment, a process for the production of novel MGS's is provided. In one embodiment, the process enables the production of the MGS's along with efficient extraction of proteins from a plant biomass and sugar precursors (carbohydrates) used for production of ethanol. Embodiments of the present invention relate to a process for producing a microbial growth stimulant solution (MGSs) from a lignocellulosic plant biomass comprising: (a) providing a harvested lignocellulosic plant biomass; (b) treating the plant biomass with an Ammonia Fiber Expansion (AFEX) process to provide a treated plant biomass; (c) extracting proteins in the treated plant biomass with an aqueous alkaline ammonium hydroxide solution comprising up to about 3% by weight $NH_4OH$ to provide the extracted proteins in the solution; and (d) separating at least some of the proteins and part of the ammonia from the solution to thereby produce a microbial growth stimulant solution. In one embodiment, the plant is a monocot, such as wheat, rice, maize or switchgrass, although the invention is not so limited.

In one embodiment, the pH in step (c) is above about 8 and the proteins are separated from the solution by precipitation or ultrafiltration. In one embodiment, the extracting of the proteins in step (c) is after a hydrolysis step in the plant biomass, after step (b), to produce sugars from sugar precursors in the biomass. In an alternative embodiment, the extracting of the proteins in step (c) is before a hydrolysis step in the plant biomass, after step (b), to produce sugars from sugar precursors in the biomass and optionally in addition extracting after the hydrolysis step.

Embodiments of the present invention also relate to a process for producing a microbial growth stimulant solution from a lignocellulosic plant biomass comprising: (a) providing a harvested lignocellulosic plant biomass; (b) treating the plant biomass with an Ammonia Fiber Expansion (AFEX) process to provide a treated plant biomass; (c) soaking the treated plant biomass in an alkaline aqueous solution of ammonium hydroxide at 25° to 70° C. to provide a soaked plant biomass in the solution; (d) extracting the solution from the soaked plant biomass in step (c); (e) separating at least some of the crude proteins and ammonia from the solution of step (d) from the plant biomass; and (f) retaining the solution as the microbial growth stimulant solution. Further still, a pH in step (c) is above about 8. Still further, the proteins are separated from the solution in step (e) by precipitation or ultrafiltration. Further still, the proteins are separated in step (e) after a hydrolysis step in the plant biomass, after step (b), to produce sugars from carbohydrates in the biomass. Finally, the proteins are separated in step (e) before a hydrolysis step in the biomass, after step (b), to produce sugars from carbohydrates in the biomass and optionally in addition extracted after the hydrolysis step.

As discussed in '020901, proteins from lignocellulosic biomass, such as grasses, can provide an economic benefit to biorefineries by providing a valuable co-product to ethanol processing. In the embodiments discussed herein, a process for extracting these proteins in line before the ethanol production, and after a pretreatment, such as an Ammonia Fiber Explosion Expansion (AFEX) pretreatment, is provided. The grasses are, in particular, extracted with a relatively dilute aqueous ammonium hydroxide solution. The extract can undergo enzymatic hydrolysis to convert its cellulose and hemicellulose to simple sugars before or after the removal of the proteins. After hydrolysis, the proteins released during this step are separated from the sugars by any suitable type of membrane filtration, such as ultrafiltration or precipitation, although the invention is not so limited. The remaining solid residue can undergo a simulated crossflow extraction using an aqueous ammonia solution as the solvent, where the remaining protein is recovered. This process can remove up to 99% of the protein from the biomass, indicating a high yield is attainable. The ammonia used can be recycled into the AFEX process. The protein extract is sold as animal feed or recycled back into hydrolysis. As indicated in this application, the solution remaining after the protein extraction is an MGS.

As noted herein, the growth stimulant is produced as a result of protein extraction. In one embodiment, a process for extracting plant proteins from a lignocellulosic plant biomass is provided, comprising: (a) providing a harvested lignocellulosic plant biomass; (b) treating the plant biomass with an Ammonia Fiber Expansion (AFEX) process to provide a treated plant biomass; and (c) extracting proteins in the treated plant biomass with an aqueous alkaline ammonium hydroxide solution comprising up to about 3% by weight $NH_4OH$ to provide the extracted proteins in the solution. In one embodiment, the pH is above about 8. Further still, the proteins can be separated from the solution by precipitation or ultrafiltration. Further, the extracting is after a hydrolysis step in the plant biomass, after step (b), to produce sugars from sugar precursors in the biomass. Still further, the extracting of the proteins is before a hydrolysis step in the plant biomass, after step (b), to produce sugars from sugar precursors in the biomass and optionally in addition after the hydrolysis step.

In another embodiment, a process for isolating plant proteins from a lignocellulosic plant biomass, is provided, comprising: (a) providing a harvested lignocellulosic plant biomass; (b) treating the plant biomass with an Ammonia Fiber Expansion (AFEX) process to provide a treated plant biomass; (c) soaking the treated plant biomass in an alkaline aqueous solution of ammonium hydroxide at 25° to 70° C. to provide a soaked plant biomass in the solution; (d) extracting the solution from the soaked plant biomass in step (c); and (e) separating crude proteins from the solution of step (d) so as to provide isolated plant proteins from the plant biomass. In one embodiment, the pH is above about 8. Still further, the proteins are separated from the solution by precipitation or ultrafiltration. Further still, the proteins are separated after a hydrolysis step in the plant biomass, after step (b), to produce sugars from structural carbohydrates in the biomass. Finally, preferably the proteins are separated before a hydrolysis step in the biomass, after step (b), to produce sugars from structural carbohydrates and optionally in addition after the hydrolysis step.

In another embodiment, the proteins are extracted with an aqueous ammonium hydroxide solution. As with the dilute aqueous ammonium hydroxide solution, the extract can undergo enzymatic hydrolysis to convert its cellulose and hemicellulose to simple sugars before or after the removal of the proteins, with the process continuing as described above. In one embodiment, the recovered ammonia can be recycled into the AFEX process. In one embodiment, the protein extract is sold as animal feed or recycled back into hydrolysis.

By disrupting the lignocellulosic structure of the biomass, proteins appear to more easily diffuse out of the biomass and into the solution. In one embodiment, sugar and protein yields are further increased using further integration of pretreatment, extraction, and/or hydrolysis. Removing soluble material during extraction can remove hydrolysis inhibitors, whereas hydrolysis of the cellulose and hemicellulose can further improve protein recovery. One (1) particular advantage of integration is in the use of a dilute ammonia solution as an extraction agent. A portion of the ammonia used in the AFEX process can be diluted and used as the extraction solution before returning to the ammonia recovery system, potentially lowering overall raw material requirements.

To summarize, lignocellulosic biomass is an economical and abundant carbon source which can be converted to various fuels and chemicals through fermentation. Under the current conventional biorefining approach, the production of a fermentable sugar mixture requires saccharolytic enzymes, commercial nutrient supplements and detoxification. The costs associated with these three steps, which are projected at 45% of the total processing cost, must be reduced to improve overall economics of cellulosic biofuels.

Ammonia fiber expansion (AFEX), for example, produces reactive, highly fermentable plant materials by reducing inhibitory degradation product generation and enriching the nitrogen content of the pretreated materials. In one embodiment, an integrated cellulosic biorefinery approach is provided which features ethanol, enzyme and yeast production based on AFEX-pretreated corn stover.

In a specific embodiment, the nutrient content (protein, vitamins and trace elements) of the AFEX-corn stover enzymatic hydrolysate is at high solids loading (18%). In one embodiment, a process design is provided which supports both ethanol and in-house enzyme production using AFEX-pretreated corn stover. In an additional embodiment, a comparative economic modeling study is provided relative to the conventional approaches. The inventors are therefore the first to demonstrate a new paradigm in which AFEX-pretreated biomass, without washing, detoxification or nutrient supplementation, can serve as the source of carbon, nitrogen and other nutrients for the biorefinery.

Embodiments of the invention will be further described by reference to the following examples, which are offered to further illustrate various embodiments of the present invention. It should be understood, however, that many variations and modifications may be made while remaining within the scope of the present invention.

Example 1

The feasibility of extracting proteins from switch grass harvested in the spring while simultaneously producing sugars through enzymatic hydrolysis was examined. Conditions for solid/liquid extraction using aqueous ammonia were optimized and compared to other solvents. Potential process flow schemes were examined with respect to their sugar and protein yields before a complete material balance of the final process was determined. The solution after removal of some of the proteins and ammonia is the MGS.

Materials and Methods

Feedstock

The feedstock used in this experiment was Alamo switchgrass obtained from Auburn University and harvested on May 22, 2005. The moisture content of the material was approximately 9%. All material was ground to less than 2 mm prior to experiments.

Pretreatment

The AFEX pretreatment was performed in a 300 mL stainless steel pressure vessel. Water was mixed with the switchgrass to increase the moisture content to 80% dry weight basis. Glass spheres were added to minimize void space, thereby reducing the amount of ammonia in the gaseous state. The lid was bolted shut, and a sample cylinder loaded with 1 (+/−0.04) g $NH_3$ per g dry biomass, allowing the ammonia to be charged into the vessel. The reactor was heated using a 400 W PARR heating mantle, and allowed to stand at 100° C. (+/−1° C.) for five minutes. The pressure was explosively released by rapidly turning the exhaust valve. The treated samples were removed and were placed in a fume hood overnight to remove residual ammonia.

Hydrolysis

The enzymatic hydrolysis procedure was based upon the LAP-009 protocol from the National Renewable Energy Laboratory (19). Samples were hydrolyzed in Erlenmeyer flasks at 10% solid loading buffered to pH 4.8 by 1M citrate buffer. Spezyme CP (Genencor; Palo Alto, Calif.) cellulase was loaded at 15 FPU/g glucan (31 mg protein/g glucan), and J3-glucosidase (Novozyme 188; Bagsvaerd, Denmark) at 64 pNPGU/g glucan. All samples were incubated at 50° C. with 200 rpm rotation. Sugar concentration after 168 hours was determined using a Waters High Performance Liquid Chromatograph (HPLC) system equipped with a Bio-Rad (Richmond, Calif.) Aminex HPX-87P carbohydrate analysis column. Degassed HPLC water with a flow rate of 0.6 mL/min was used as the mobile phase, while the temperature in the column was kept constant at 85° C.

Protein Extractions

Screening for optimal protein extraction conditions was done using a Dionex (Sunnyvale, Calif.) ASE 200 Accelerated Solvent Extractor. Extractions were performed at 1500 psi, which reduces the required residence time from 30 to 3 minutes. Extractions were done using 11:1 (w/w) liquid/solid ratio and two (2) separate extractions per sample. For experiments involving varying the pH, hydrochloric acid was used to reduce the pH. The pH of the solution was measured after the extraction was complete. Once the optimal extraction conditions were obtained, all further extractions were performed in flasks for 30 minutes with a 10:1 liquid/solid ratio while continuously stirred.

Due to the presence of ammonia nitrogen, both during the AFEX pretreatment and subsequent extractions, it is impossible to use standard nitrogen analysis methods (the Kjeldahl or Dumas methods) to measure total protein content. Instead, protein concentration was measured using a Pierce (Rockford, Ill.) bichronimic acid colorimetric assay kit using bovine serum albumin (BSA) as a standard. To reduce the effects of interfering agents such as ammonium salts, lignin components, and glucose, the proteins were first precipitated and resolubilized (20). A 100 µl, 0.15% sodium deoxycholate was added to 100 μl, protein solution and allowed to sit for 15 minutes. 200 μL of 15% trichloroacetic acid solution was added, and allowed to sit at 2° C. overnight. The mixture was centrifuged at 13000 RPM for 10 minutes, and the resulting pellet washed with acetone. The pellet was resolubilized in a buffer solution containing 0.1M Tris, 2.5M urea, and 4% SDS. Known concentrations of protein extracts were used to calibrate the protein recovery of this method.

Composition Analysis

The weight and moisture content of the remaining solid fraction after each processing step was measured for determining the mass balance in the system. The composition of each of these fractions was determined based upon NREL's LAP 002 protocol (19). Ash content was determined by heating 1.5 g of biomass at 575° C. for 24 hours and measuring the weight loss. Water and ethanol extractives were removed using a soxhlet extraction. A portion of the extracted biomass was digested in concentrated (72%) sulfuric acid in a 10:1 liquid:solid ratio at 30° C. for one hour. The solution was diluted to 4% sulfuric and autoclaved at 120° C. for one hour, and then analyzed for sugar components using a Bio-Rad (Richmond, Calif.) Aminex HPX-87H HPLC column using sulfuric acid as the mobile phase. The acid insoluble lignin was measured as the remaining solid after hydrolysis less the ash content in the solid residue.

Results and Discussion

Composition Analysis

The composition of the switchgrass used in this study is shown in Table 1. Approximately 80% of the mass was accounted for, with the remaining material being primarily water soluble components, such as minor organic acids, and acid soluble lignin. The amount of protein present was lower than reported in the literature for other strains of switchgrass. Switchgrass grown as a biomass energy crop and harvested early in the growing season would likely have a protein contents near 10%, and thus, might be more suitable for integrated protein and sugar processing. The amount of fiber present was lower than switchgrass harvested at a later date, which seems to suggest lower sugar yields would also result from using an earlier cut. However, early cut switchgrass is less recalcitrant than that harvested in the fall, and thus, the lower cellulose and hemicellulose content may not be a significant factor. The low amount of lignin is a promising sign, as this implies less interference with hydrolysis as well as fewer harmful degradation products that could inhibit sugar production or otherwise be present in the protein product. Ash content is higher than at later harvests, as expected. It will likely be necessary to return much of this ash to the land in order to maintain a high quality soil.

Table 1 shows the composition of Alamo (g/100 g dry matter) switchgrass. AI-acid insoluble.

TABLE 1

| Component | % Value |
| --- | --- |
| Glucan | 26.4 |
| Xylan | 16.4 |
| Arabinan | 3.5 |
| Sucrose | 3.4 |
| Protein | 7.3 |
| AI Lignin | 10.8 |
| Lipids | 7.3 |
| Ash | 4.8 |
| Total | 79.9 |

The essential amino acid profile for switchgrass, along with literature values for corn and soy (22), is shown in Table 2. The most promising feature of switchgrass protein is the high value seen for lysine, an essential amino acid that is often the first limiting amino acid in poultry diets. High values for phenylalanine and valine are also seen. Although switchgrass is somewhat deficient in leucine, arginine, and methionine, these amino acids are relatively abundant in corn. Thus, a corn-switchgrass protein diet would balance out these deficiencies, and thus might be a strong alternative to a corn-soy diet.

Table 2 shows essential amino acid profile of Alamo switchgrass (SG) compared to literature values for soybean and corn grain (22). Values are in g amino acid/100 g protein. Of particular note are lysine, phenylalanine, and valine, of which switchgrass is rich in, and methionine, of which switchgrass is somewhat deficient.

TABLE 2

| | Arg | His | Ile | Leu | Lys | Met | Phe | Thr | Val |
| --- | --- | --- | --- | --- | --- | --- | --- | --- | --- |
| SG | 2.1 | 1.8 | 3.7 | 5.6 | 7.4 | 0.6 | 9.1 | 4.9 | 6.1 |
| Soy | 7.5 | 2.6 | 4.9 | 7.7 | 6.1 | 1.6 | 5.1 | 4.3 | 5.1 |
| Corn | 2.9 | 1.6 | 4.3 | 16.2 | 1.6 | 2.3 | 5.9 | 3.1 | 4.4 |

Extraction Optimization

FIG. 1 shows the effect of the temperature of the extraction on the overall protein and mass yields. Protein yields increased significantly from 25° C. to 40° C., but further increases in temperature did not result in major improvements in protein yield. It is likely that most, if not all, of the proteins present in the switchgrass are in their natural state, as the harvesting and drying conditions should not have damaged them. As such, the mild temperatures should not unfold the proteins or significantly affect their solubility.

Figure 2:
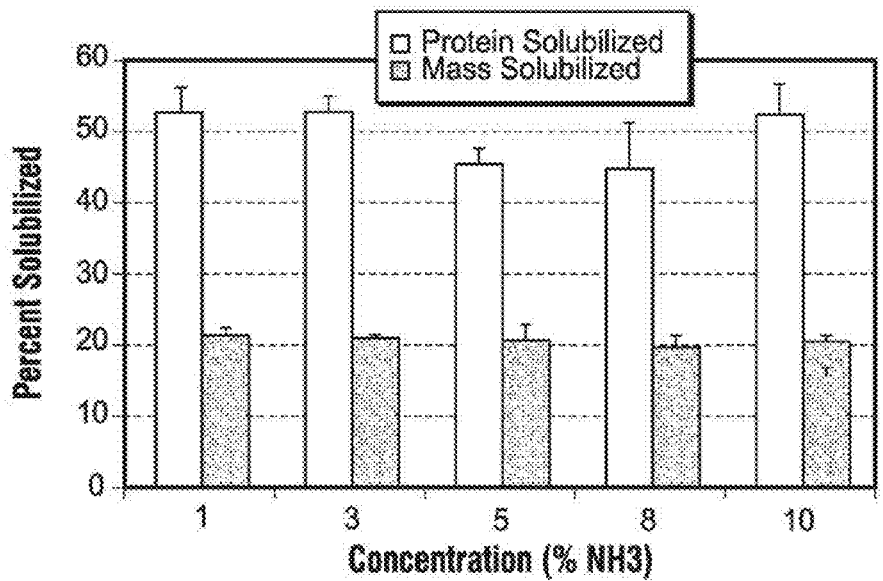
FIG. 2 is a graph showing the effect of ammonia concentration on protein yields in embodiments of the present invention. All extractions were done at 50° C. and at pH=10.5 after an AFEX treatment. The results are combined after two (2) separate extractions using 11:1 liquid/solid ratio and 3 minute residence time. All runs were done in duplicate and error bars represent the maximum and minimum values.

The effect of ammonia concentration on extraction yields is seen in FIG. 2. Protein yield remains constant from 1-3% $NH_4+$, but then begins to drop off. This is most likely due to "salting out" the protein, as the increase in salt concentration decreases the amount of water available to solubilize the protein. There does not appear to be any salting in effect, likely because 1% salt solution is already a sufficient concentration to solubilize the protein. The total mass solubilized was unaffected by salt concentration, as expected.

Figure 3:
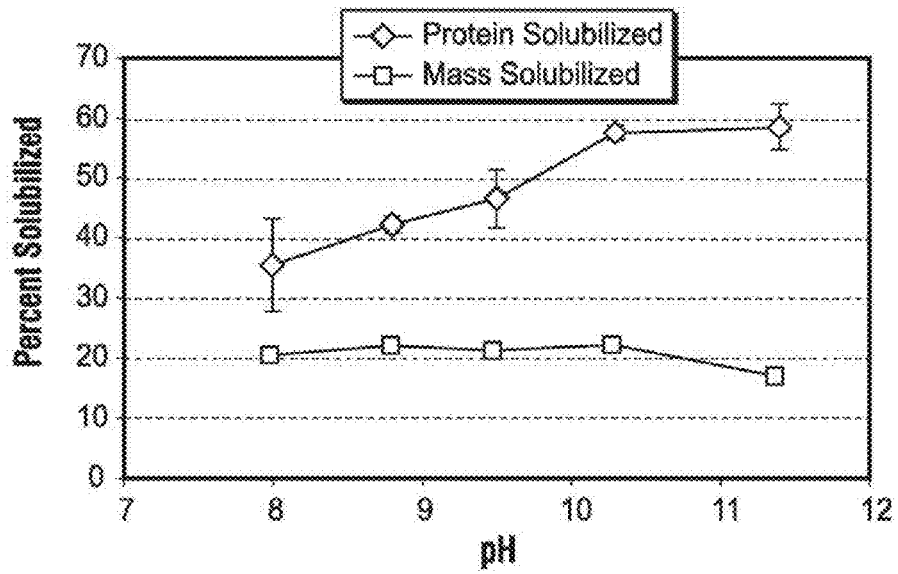
FIG. 3 is a graph showing the effect of extraction pH on protein yields in embodiments of the present invention. All extractions were done with 3% ammonium hydroxide and at 25° C. The results are combined after two (2) separate extractions using 11:1 liquid/solid ratio and 3 minute residence time. All runs were done in duplicate and error bars represent the maximum and minimum values.

The most significant factor in determining protein yields is the pH of the system, as seen in FIG. 3. The amount of protein extracted increased dramatically from a pH of 8 to 10.5 before leveling off. Similar trends have been seen in other types of biomass (10-16). Most proteins have an acidic isoelectric point, the pH at which the protein will have no net charge and therefore, be the least soluble in a polar medium. Thus, increasing the pH should increase protein solubility, as demonstrated here. The most alkaline solution also produced a significant drop in the total mass solubilized, a potentially useful characteristic. If there is less biomass in solution, it should be easier to purify the proteins. In addition, the biomass lost during extraction likely includes hemicellulose that could be hydrolyzed into sugars for ethanol production. Further increases in pH would require a stronger base than ammonia and might degrade the protein, and thus were not considered.

Figure 4:
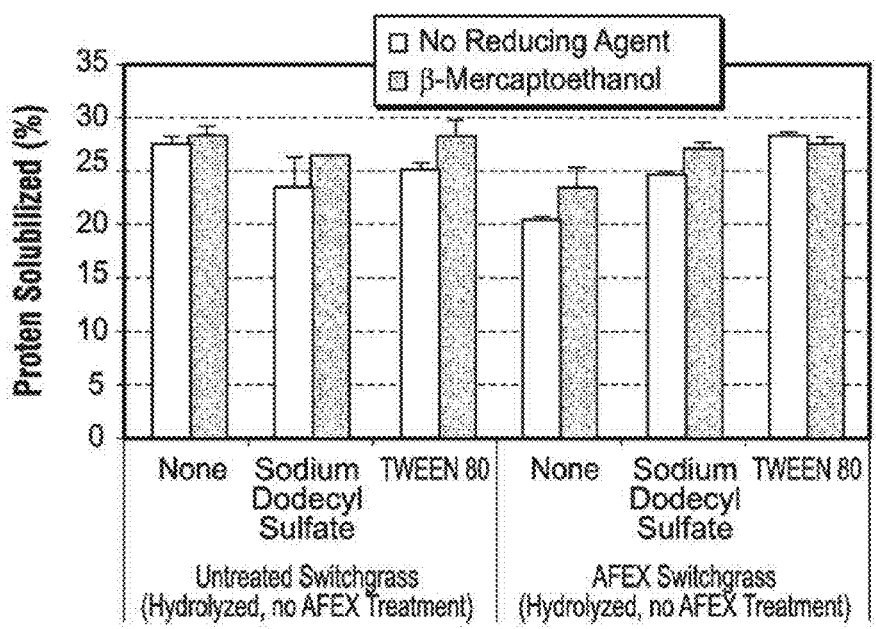
FIG. 4 is a graph showing effect of reducing agents on protein yields for untreated and AFEX treated samples in embodiments of the present invention. All extractions were done with 3% ammonia by weight, 25° C., and at pH=10.5. The results are combined after two (2) separate extractions using 11:1 liquid/solid ratio and 30 minute residence time. Both the ionic sodium dodecyl sulfate (SDS) and the nonionic Tween 80 (Tw80) surfactants were tested, both with and without the addition of β-mercaptoethanol. All runs were done in duplicate and error bars represent the maximum and minimum values.

As seen in FIG. 4, attempts were made to improve yields by the addition of the nonionic surfactant Tween 80, the ionic surfactant sodium dodecyl sulfate (SDS), and β-mercaptoethanol, a reducing agent. No significant improvements can be found by the addition of either surfactant or reducing agent for the untreated switchgrass. However, adding β-mercaptoethanol and Tween 80 to AFEX treated grass did increase protein removal. This would seem to suggest that the AFEX process affects the proteins in some manner. This effect might be through the creation of sulfur-sulfur bonds, which would then be cleaved by β-mercaptoethanol, or by proteins unfolding and exposing hydrophobic sites, which can be resolubilized with surfactants. The total mass solubilized also increased with the addition of surfactants, such as Tween 80, most likely due to interactions between the surfactants and hydrophobic portions of the biomass.

Figure 5:
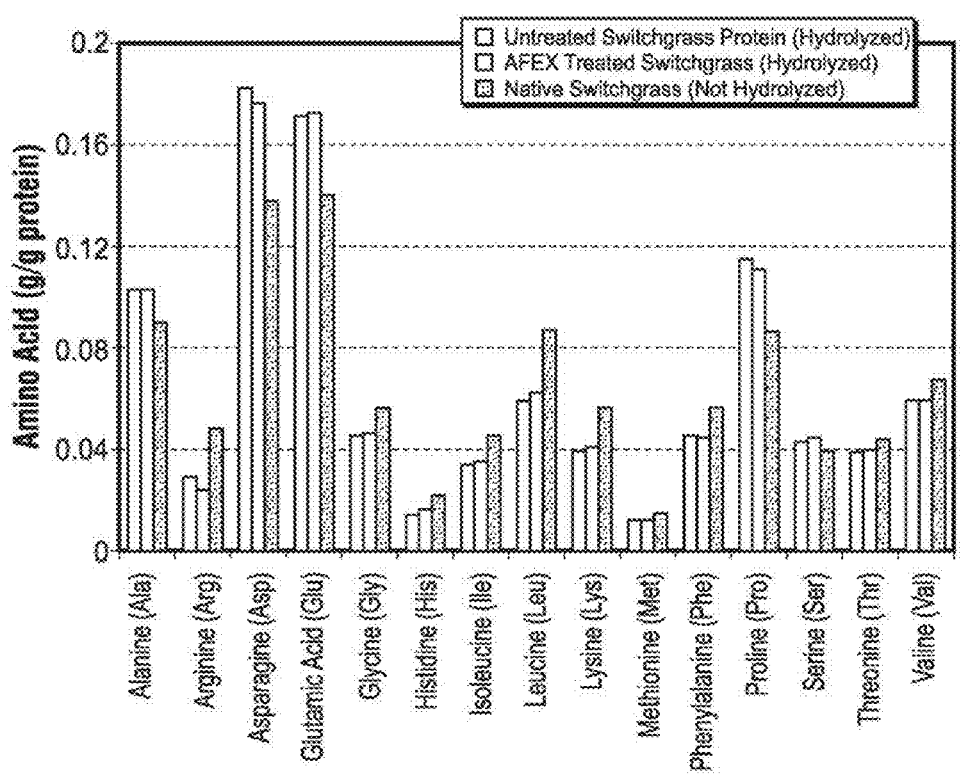
FIG. 5 is a graph showing amino acid profiles for untreated protein extract, AFEX treated protein extract, and the native switch grass protein in embodiments of the present invention.

To determine whether AFEX pretreatment affects the types of proteins recovered, the composition of the individual amino acids was determined, as seen in FIG. 5. Both the untreated and AFEX treated samples were extracted at the optimal ammonia conditions without adding surfactant or reducing agent. Although the amino acid profile for the proteins solubilized during extraction compared to the total protein from switchgrass is quite different, there is very little difference between extractions from untreated and AFEX treated grass. Although AFEX does disrupt the cellular structure of the biomass, it does not appear to release any other proteins to be available for extraction. Therefore, it appears that the structure of the plant is not a major hindrance in protein recovery, but rather the structure of the protein itself.

Thus, optimal extraction conditions for switchgrass are approximately 3% aqueous ammonia at a pH of 10 and temperature of 40-50° C. These conditions are in line with those seen for protein extraction of other types of biomass, and are the conditions used for all subsequent experiments reported here. Total protein yields are approximately 40%. However, AFEX did not appear to significantly improve yields of protein, unlike previously reported with coastal Bermuda grass and sodium hydroxide (17).

Integration

Two (2) potential scenarios for integrated sugar and protein recovery were studied: an extraction immediately after AFEX and an extraction immediately after hydrolysis. A third option, extraction prior to AFEX, produced sugar yields far below the first two scenarios, and so is not presented here. It is possible that extracting proteins and other material prior to AFEX changes the effects of AFEX pretreatment. AFEX produces some organic acids that may inhibit hydrolysis, and it is possible that a prior extraction could produce more of these inhibitory acids. Washing the biomass after AFEX increased the sugar yields to approximately the same level as hydrolysis without any previous extraction. However, this process was deemed to require too much water use with no clear advantage, and thus was not studied in greater depth.

Figure 6A:
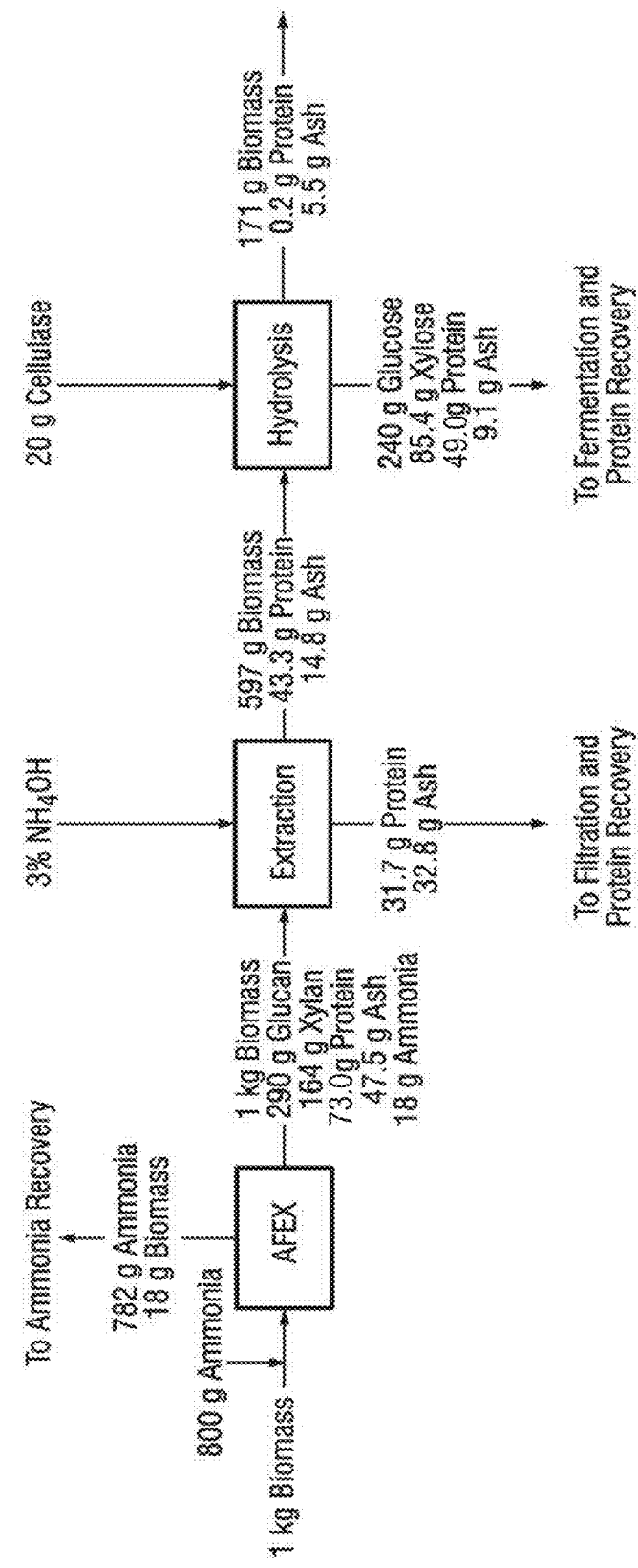
FIG. 6A is a process flow diagram for AFEX treatment with extraction prior to hydrolysis in embodiments of the present invention. Balances around the protein and ash content are given, as well as total mass and the amount of glucose and xylose produced.

The overall mass balance for integrated sugar and protein with extraction prior to hydrolysis is seen in FIG. 6A. Final yields were 240 g glucose, 85.4 g xylose, and 80.7 g protein per kg dry biomass. Sugar recovery was approximately 74% of theoretical values, indicating further improvements in sugar recovery can be made. Approximately 40% of the protein was found in the extract and 60% in the hydrolysate, demonstrating that protein must be recovered from both streams in order to be economical. It should be noted that the insoluble biomass was washed after hydrolysis to insure all soluble components were recovered, and thus this may have acted as a second extraction to remove any remaining proteins bound to insoluble portions of the biomass. Total protein yield is approximately 87% of the total, taking into account both the switchgrass protein and the enzymes used in hydrolysis. However, virtually no insoluble protein remains in the biomass, thus suggesting that the remaining protein was broken down and lost at some point during the process.

Approximately 40% of the biomass is solubilized during the initial protein extraction step. The soluble fraction of the biomass after the proteins have been removed can be used as a MGS. The protein might be concentrated and removed through ultrafiltration or heat precipitation, while the remaining solution undergoes further processing to provide the MGS.

Most of the ash was removed from the biomass during the first extraction step. It is important to remove this ash, as the final insoluble residue would likely be burned to provide heat and power for the refinery. The ash content in switchgrass, particularly potassium, has been shown to cause problems with slagging in coal/biomass co-firing power plants. The remaining biomass contains only 3% ash, and thus should reduce this risk in heat and power generation. It remains to be seen if the ash in the extraction step can be separated and returned to the land. The fact that most of the ash is removed during one unit operation should help keep the costs of any ash processing step low, as only one stream needs to be treated.

Approximately 17% of the biomass remains insoluble throughout this process. There is virtually no protein or ash still present in this residue, which is mostly composed of unhydrolyzed fiber and insoluble lignin. This material would likely be burned for heat and power generation in the refinery, thus reducing natural gas or coal requirements. The lack of protein and ash would reduce the presence of NOx formation and slagging, respectively.

Figure 6B:
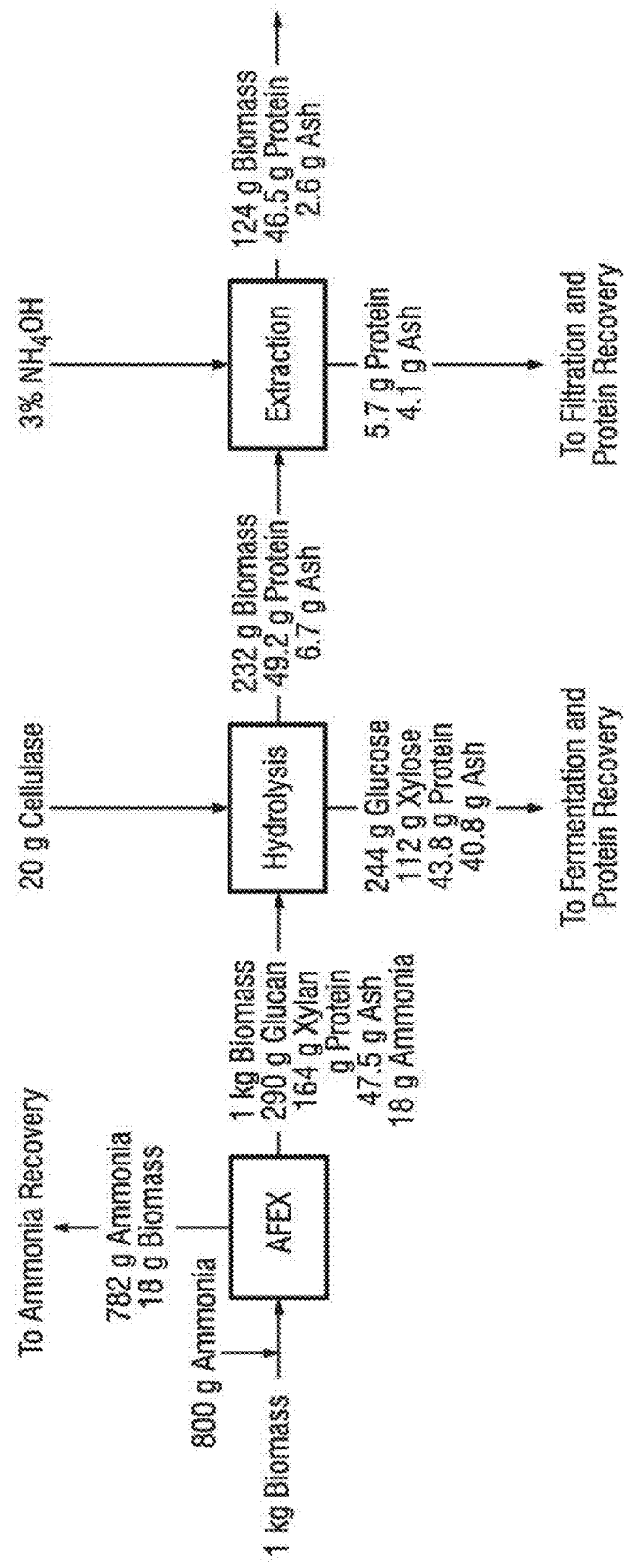
FIG. 6B is a process flow diagram for AFEX treatment with extraction after hydrolysis in embodiments of the present invention. Balances around the protein and ash content are given, as well as total mass and the amount of glucose and xylose produced.
Figure 7:
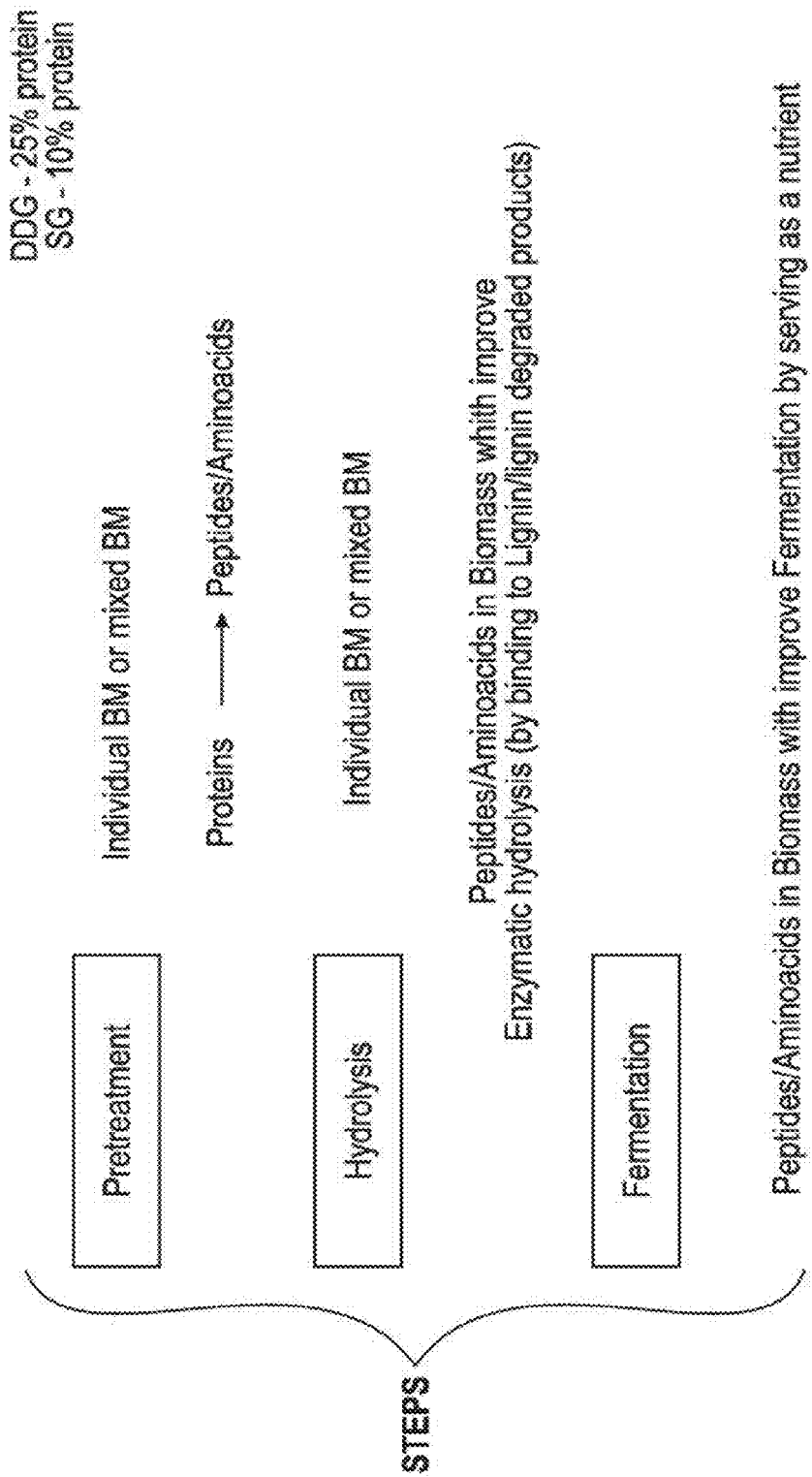
FIG. 7 is a flow chart for the use of the proteins and/or the microbial growth stimulant solution (pretreatment) in a fermentation process in embodiments of the present invention. BM is biomass, SG is Switch grass and DDG is Distillers Dried Grain.

A separate balance, focusing on performing hydrolysis prior to extraction, is shown in FIG. 6B. Here, sugar yields were slightly higher, with a total of 356 g compared to 325 g per kg biomass using the previous approach. This is mainly due to xylan conversion, indicating that xylan oligomers were likely extracted along with protein during the initial extraction step in the previous scenario. However, although approximately 60% of the protein in the switchgrass was solubilized during hydrolysis, very little was extracted afterwards. During hydrolysis, other compounds may be produced that interfere with the colorimetric analysis, thus increasing the error involved. This mass balance, however, relies solely on the individual amino acids rather than a colorimetric response, and thus is a more accurate representation of actual protein levels. Subsequent extractions on the final residue did not release more than a small fraction of the residual proteins, making it unlikely that further treatments can remove the residual protein.

The amount of insoluble material remaining is less than that of the previous scenario, indicating that less heat and power can be produced. Although less ash is present, there is still a great deal of protein remaining Protein has lower energy content than lignin and also its combustion will generate NOx. Thus, due primarily to the higher protein yields, an extraction prior to hydrolysis is preferred despite the slightly lower sugar yields.

Example 2

In this testing, solubles were extracted from AFEX treated corn stover using water to produce an aqueous extract useful as a growth medium for the cellulase enzyme-producing fungus *T. reesei*.

Figure 8:
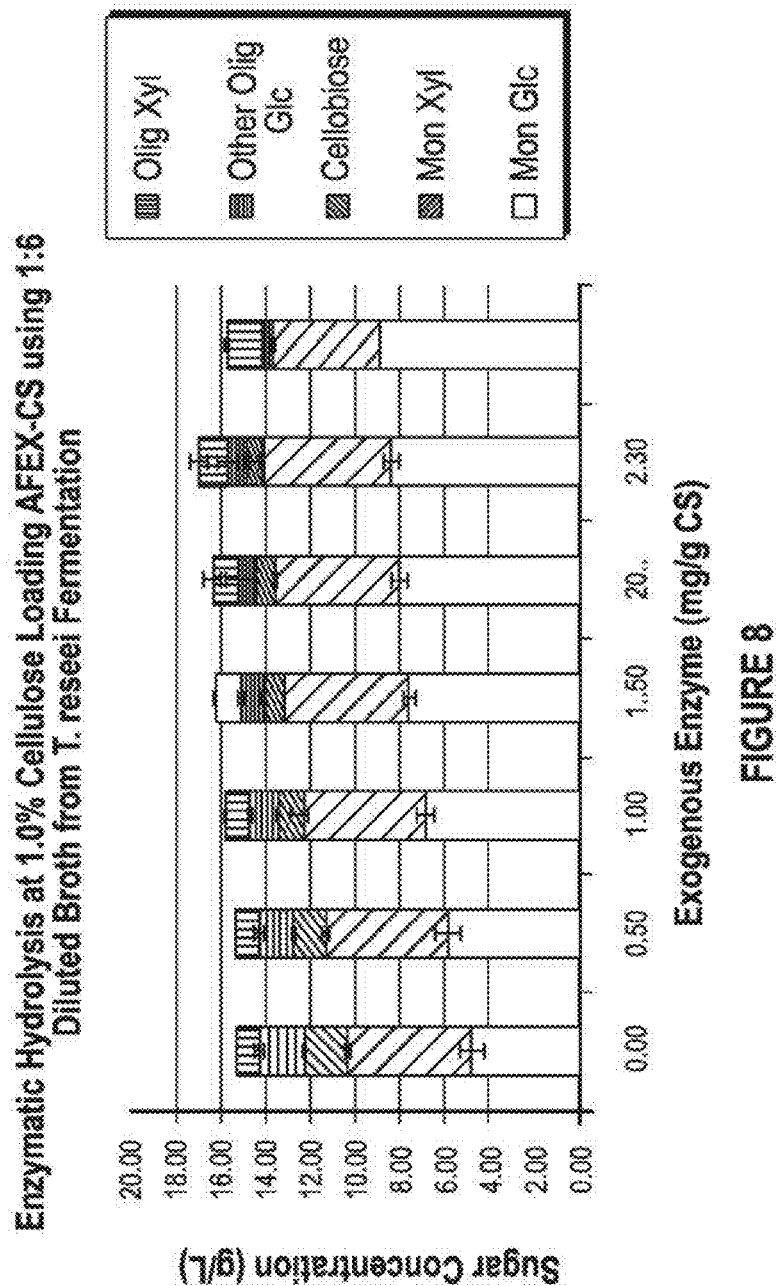
FIG. 8 shows enzymatic hydrolysis at 1.0% cellulose loading AFEX-CS using 1:6 diluted broth from *Trichoderma reesei* (hereinafter "*T. reesei*") fermentation in embodiments of the present invention.

1) Experimental Details re FIG. 8

Seed Culture Preparation

Media: 2% w/w corn steep liquor+20 g/L glucose+50 mM phosphate buffer (adjusted to pH 5.5)

Culture condition: 30° C., 200 rpm agitation, 48 hr incubation time

*Trichoderma* Fermentation

Figure 9:
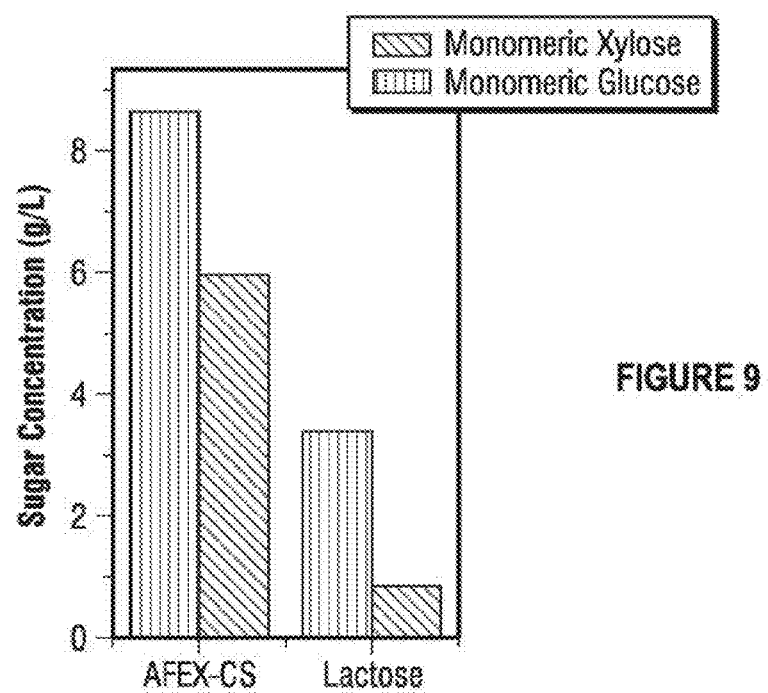
FIG. 9 shows a comparison of two induction mixture in term of their effectiveness on enzyme production and hydrolysis yield in embodiments of the present invention.
Figure 10:
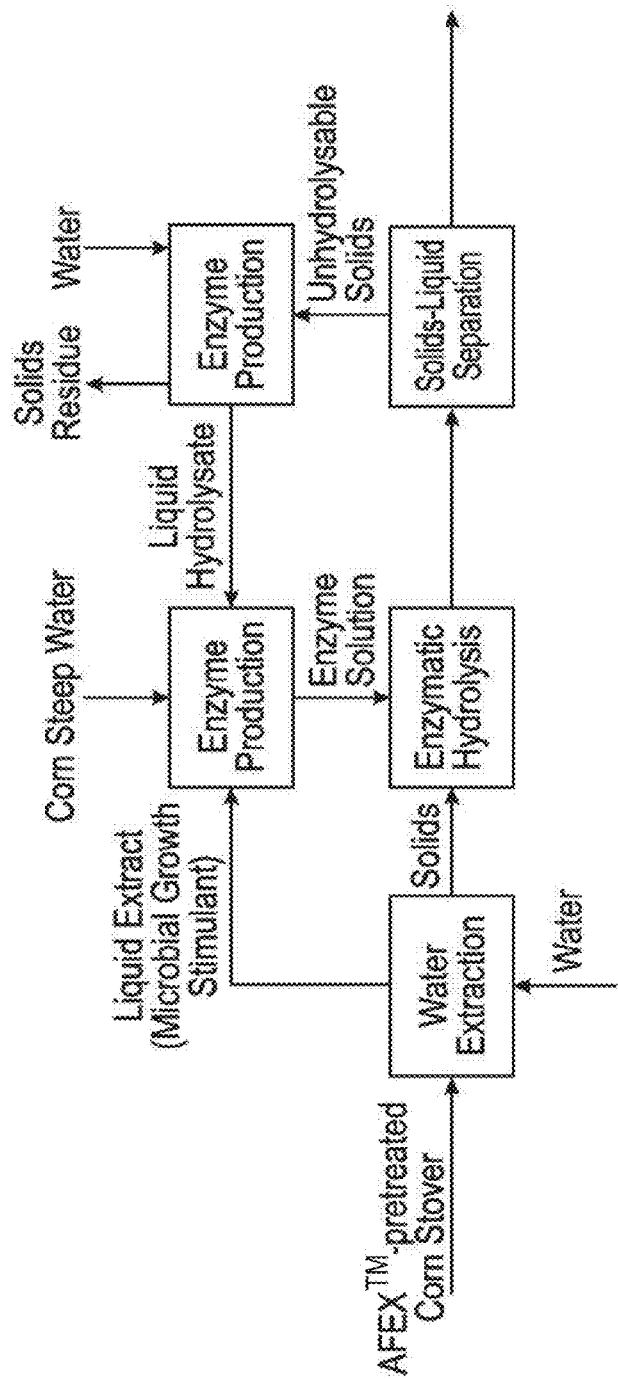
FIG. 10 shows a Proposed Integrated Cellulosic Ethanol Production with In-house Enzyme Production Utilizing Biomass as the Exclusive Source for Carbohydrates in embodiments of the present invention.
Figure 11A:
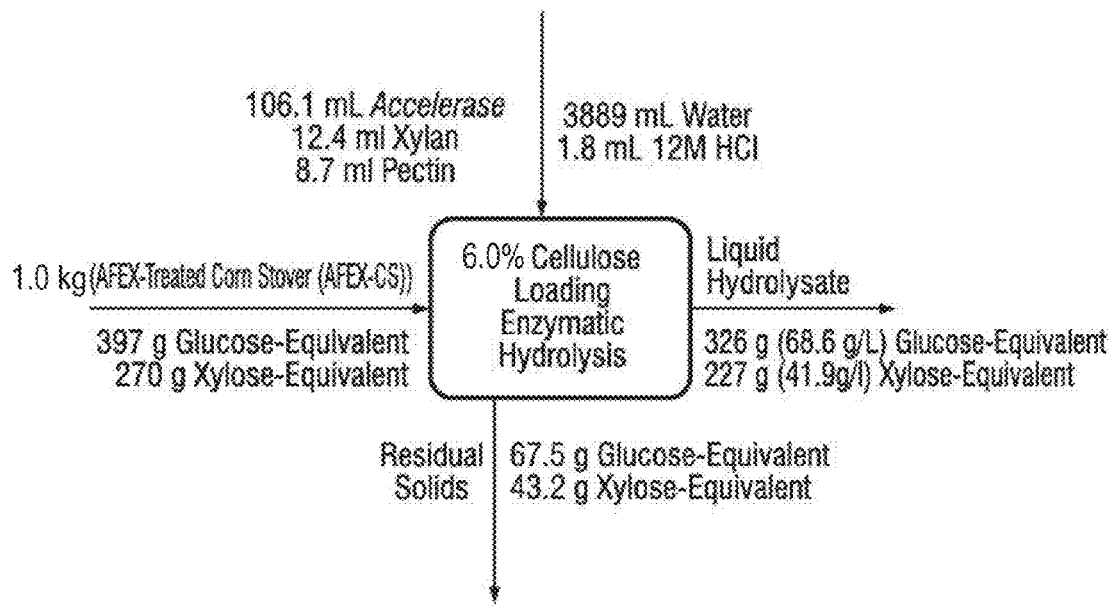
FIGS. 11A and 11B show (A) 6.0% cellulose loading solids and loading enzymatic hydrolysis and (b) AFEX and enzymatic hydrolysis in embodiments of the present invention.
Figure 11B:
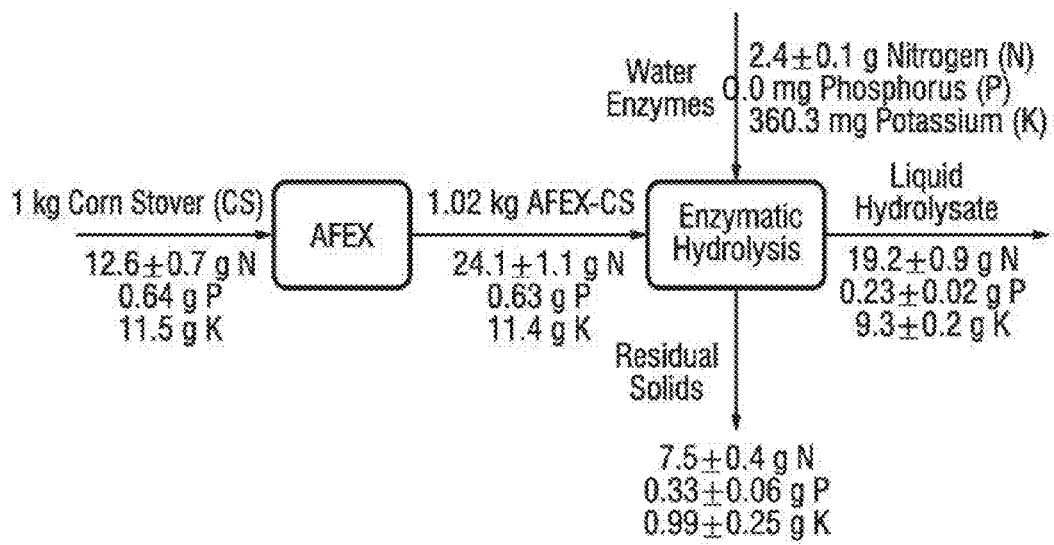
Figure 14A:
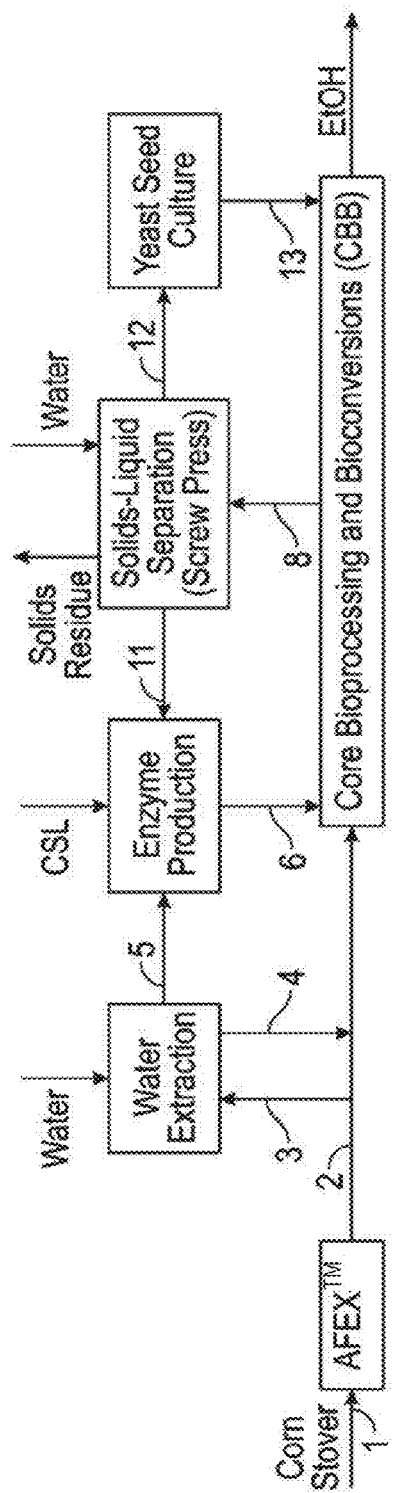
FIGS. 14A and 14B show (A) a core bioprocessing and bioconversions which includes enzyme production and (B) a subsequent fermentation step in embodiments of the present invention.
Figure 14B:
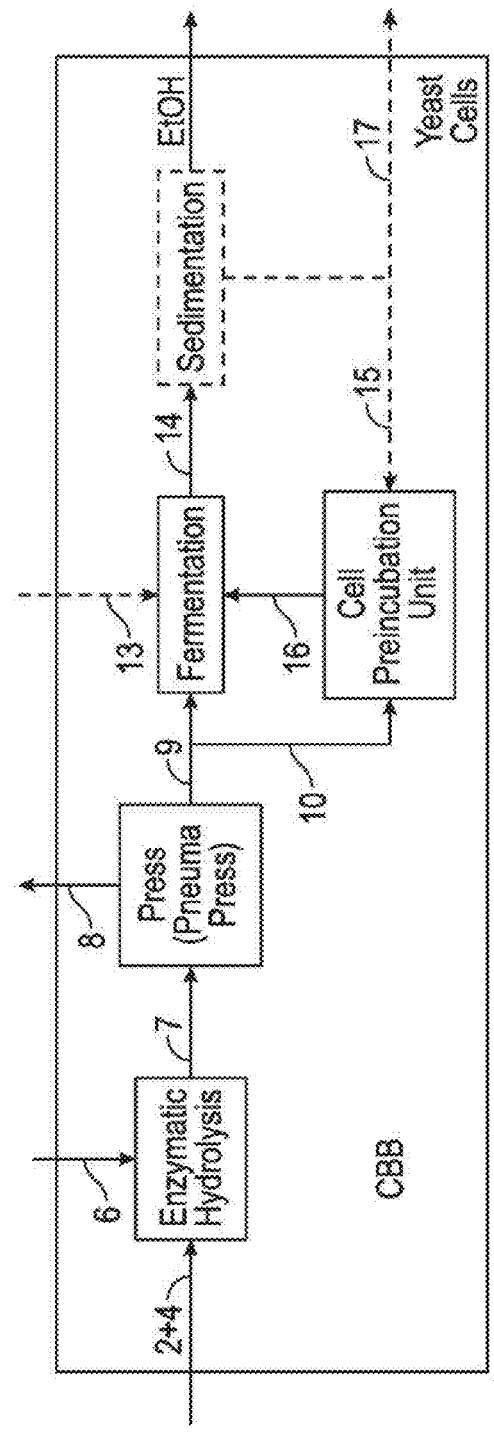

Media (proprietary mixture):
   60% v/v of seed culture+5.5% solids loading equivalent of AFEX-corn stover wash stream+0.5 g of AFEX-corn stover in 50 mL total volume
Culture Condition: pH 5.5 (adjusted every 24 hr), 30° C., 200 rpm agitation, 96 hr incubation time
Enzymatic Hydrolysis
Solids loading: 1.0% cellulose loading equivalent of AFEX-corn stover
Hydrolysis mixture: 1:6 diluted of *Trichoderma* fermentation broth with varying loading of Accellerase
Hydrolysis condition: pH 4.8, 50° C., 250 rpm agitation, 24 hr incubation time
Enzyme Quantification
   The protein present in the *Trichoderma* fermentation broth was run through a FPLC system to separate the saccharolytic enzymes from the non-saccharolytic enzymes. The protein content of the fraction, which consisted of saccharolytic enzymes, was quantified using the BCA protein assay. (See FIG. 8).
Results and Conclusions
   The *Trichoderma* broth contained 2.71±0.4 g/L saccharolytic enzymes. Using this inducer mixture, saccharolytic enzymes were produced at a high concentration sufficient for at least 18% solids loading saccharification, which required an enzyme concentration at in the range of 1.8-2.0 g/L.
Further Details
   Three different scenarios (relative to 10 mg/g standard enzyme mix: Accelerase+Multifect Xylanase+Multifect Pectinase) were tested:
1) If only soluble sugars are needed, no exogenous enzyme is needed, as the in-house enzyme is sufficient as it is.
2) If monomers and cellobiose are needed (some non-saccharolytic organism can uptake cellobiose), add 1.0 mg/g of exogenous enzyme.
3) If only monomers are needed, add about 1.5-2.0 mg/g of exogenous enzyme.
(2) Experimental Details re FIG. 9
Seed Culture Preparation
Media: 2% w/w corn steep liquor+20 g/L glucose+50 mM phosphate buffer (adjusted to pH 5.5)
Culture condition: 30° C., 200 rpm agitation, 48 hr incubation time
*Trichoderma* Fermentation
Media (proprietary mixture):
   60% v/v of seed culture+5.5% solids loading equivalent of AFEX-corn stover wash stream
Media (lactose): 60% v/v of seed culture+5.4 g/L lactose
Culture Condition: pH 5.5 (adjusted every 24 hr), 30° C., 200 rpm agitation, 96 hr incubation time
Note: The proprietary mixture contained 5.4 g/L of sugars.
Enzymatic Hydrolysis
Solids loading: 1.0% cellulose loading equivalent of AFEX-corn stover
Hydrolysis mixture: 1:6 diluted of *Trichoderma* fermentation broth with varying loading of Accellerase
Hydrolysis condition: pH 4.8, 50° C., 250 rpm agitation, 24 hr incubation time
See FIG. 9, which shows a comparison of two induction mixtures in terms of their effectiveness on enzyme production and hydrolysis yield.
Conclusion
   The proprietary mixtures are 2.5 (for glucose) to 7 times (for xylose) more potent than that from lactose.
See FIG. 10 which shows a proposed integrated cellulosic ethanol production system with in-house enzyme production utilizing biomass as the exclusive source for carbohydrates, in one embodiment of the invention.
   The results show that the estimated cost of enzymes to produce a highly fermentable sugar mixture can be reduced to the point where the enzyme cost is no longer the dominant cost of biofuel production.
See also the following:
   FIGS. 11A and 11B show (A) 6.0% cellulose loading solids and loading enzymatic hydrolysis and (B) AFEX and enzymatic hydrolysis in embodiments of the present invention.
   FIG. 12 shows a chart of total protein and free AA for various constituents in embodiments of the present invention.
   FIG. 13 shows trace element and vitamin content of AFEX-corn stover hydrolysate at 18% solids loading in an embodiment of the present invention.
   FIGS. 14A and 14B show (A) a core bioprocessing and bioconversions which includes enzyme production and (B) a subsequent fermentation step in embodiments of the present invention. See Table 3 below for additional details on FIGS. 14A and 14B.

TABLE 3

Details on Streams in FIGS. 14A and 14B

| Stream | Description |
| --- | --- |
| 1 | Untreated Corn Stover |
| 2 | AFEX-pretreated corn stover (AFEX-CS); |
| 3 | AFEX-pretreated corn stover (AFEX-CS); 10% of the total output AFEX-CS by weight |
| 4 | Washed AFEX-CS; Moisture Content at 75% |
| 5 | Water extract of AFEX-CS at 18% solids loading |
| 6 | Saccharolytic enzyme from *Trichoderma reesei* fermentation |
| 7 | Enzymatic hydrolysate in slurry |
| 8 | Moist residual solids |
| 9 | Liquid enzymatic hydrolysate |
| 10 | Split Stream of liquid enzymatic hydrolysate; 20% of Stream 9 by volume |
| 11 & 12 | Diluted AFEX-CS Hydrolysate; Sugar concentration at 30% that of Stream 9 |
| 13 | Native or recombinant *Saccharomyces cerevisiae* 424A(LNH-ST) |
| 14 | Beer stream at 4% w/v ethanol |
| 15 | Recombinant cell recycle (ethanol fermentation) for 1 hr |
| 16 | Recombinant cell recycle after preincubation in AFEX-CS hydrolysate |
| 17 | Yeast purge stream |

Figure 15:
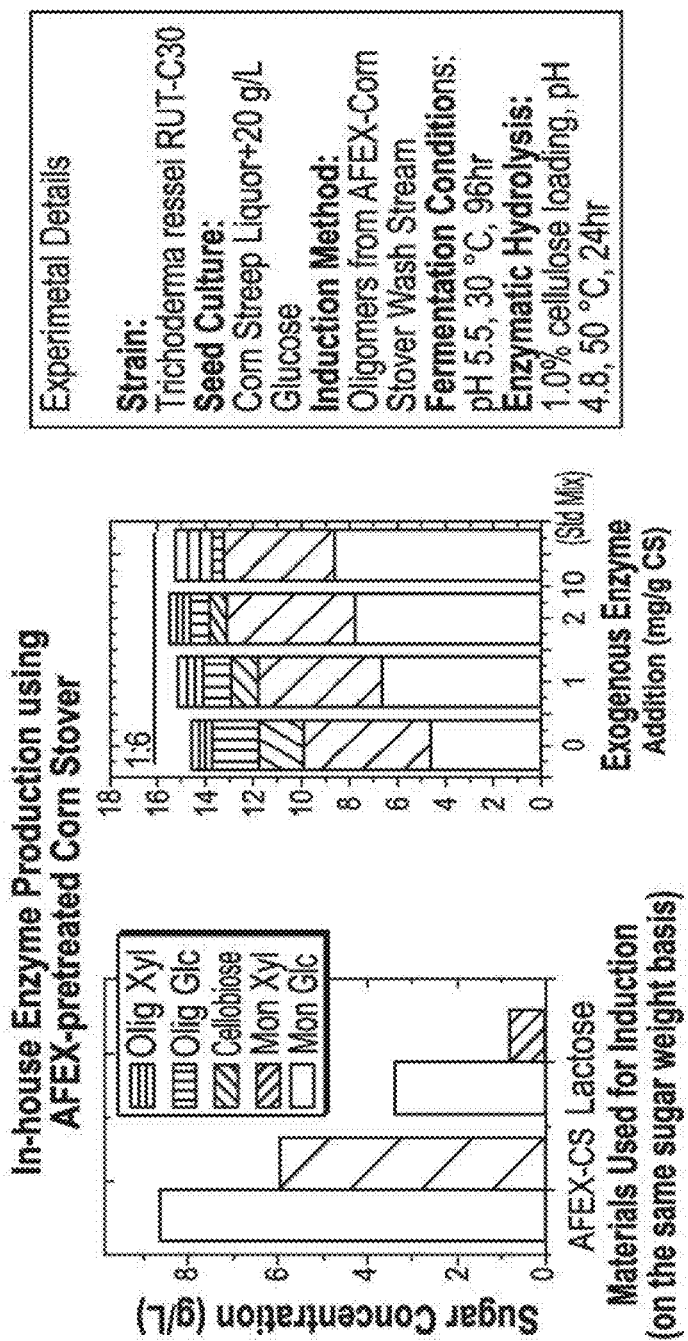
FIG. 15 shows in-house enzyme production using AFEX-pretreated corn stover in an embodiment of the present invention.
Figure 17A:
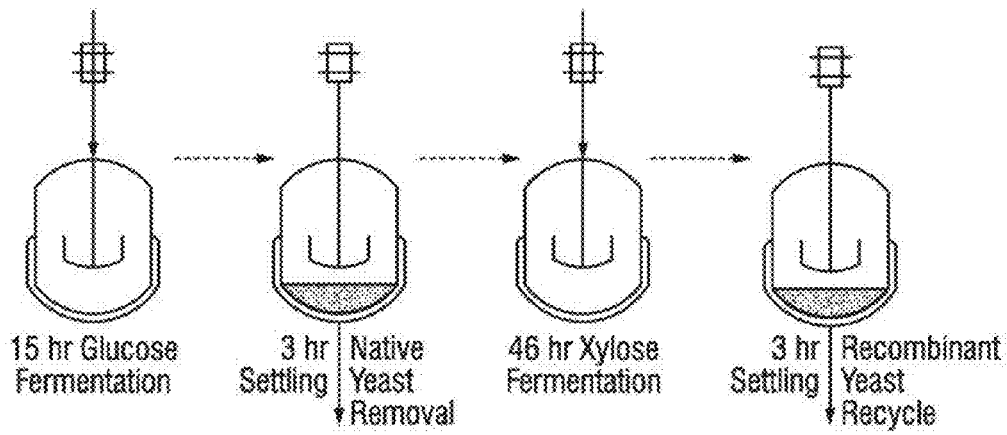
FIG. 17A shows a first portion of an exemplary fermentation process in an embodiment of the present invention.
Figure 17B:
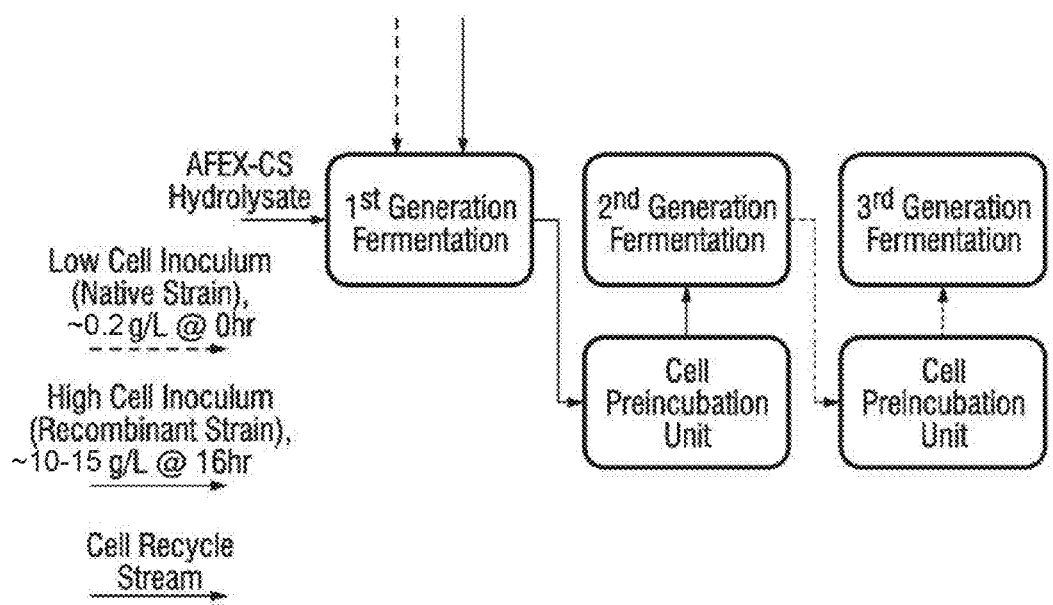
FIG. 17B shows a second portion of an exemplary fermentation process in an embodiment of the present invention.
Figures 18, 19:
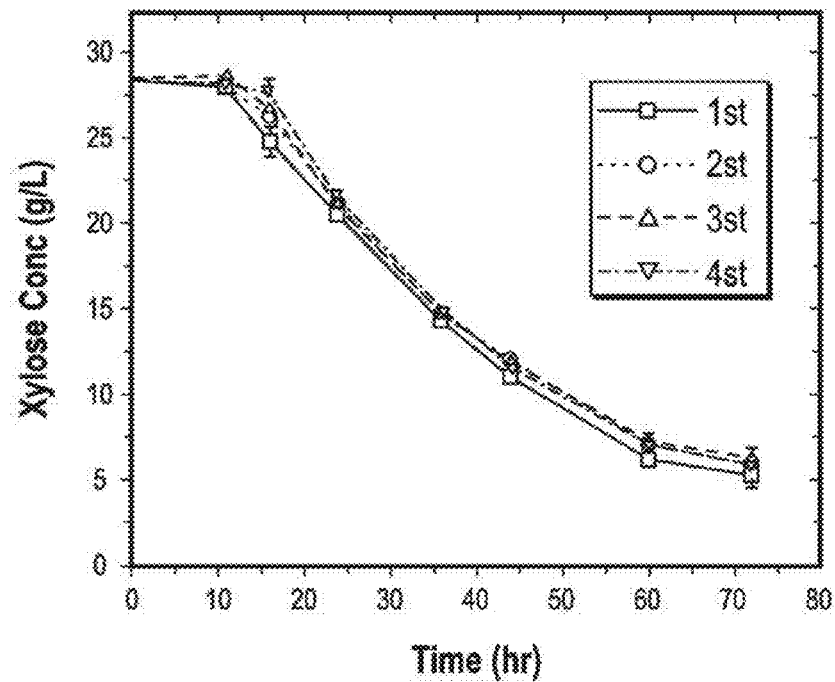
FIG. 18 shows a graph of xylose concentration over time in embodiments of the present invention.
FIG. 19 provides relevant conclusions pertinent to one or more of FIGS. 17A, 17B and 18 in embodiments of the present invention.
Figure 20A:
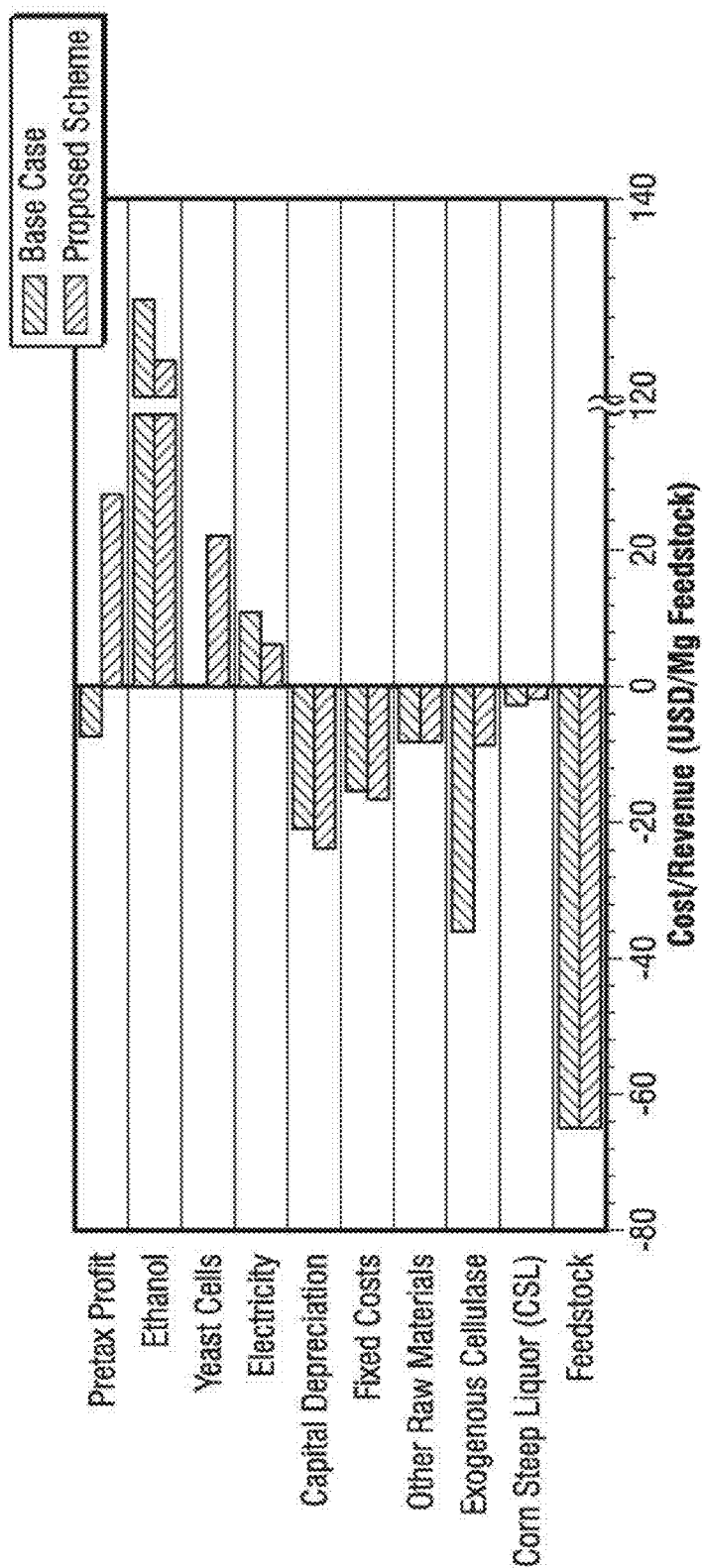
FIG. 20A shows a comparison cost/revenue study in an embodiment of the present invention.
Figure 20B:
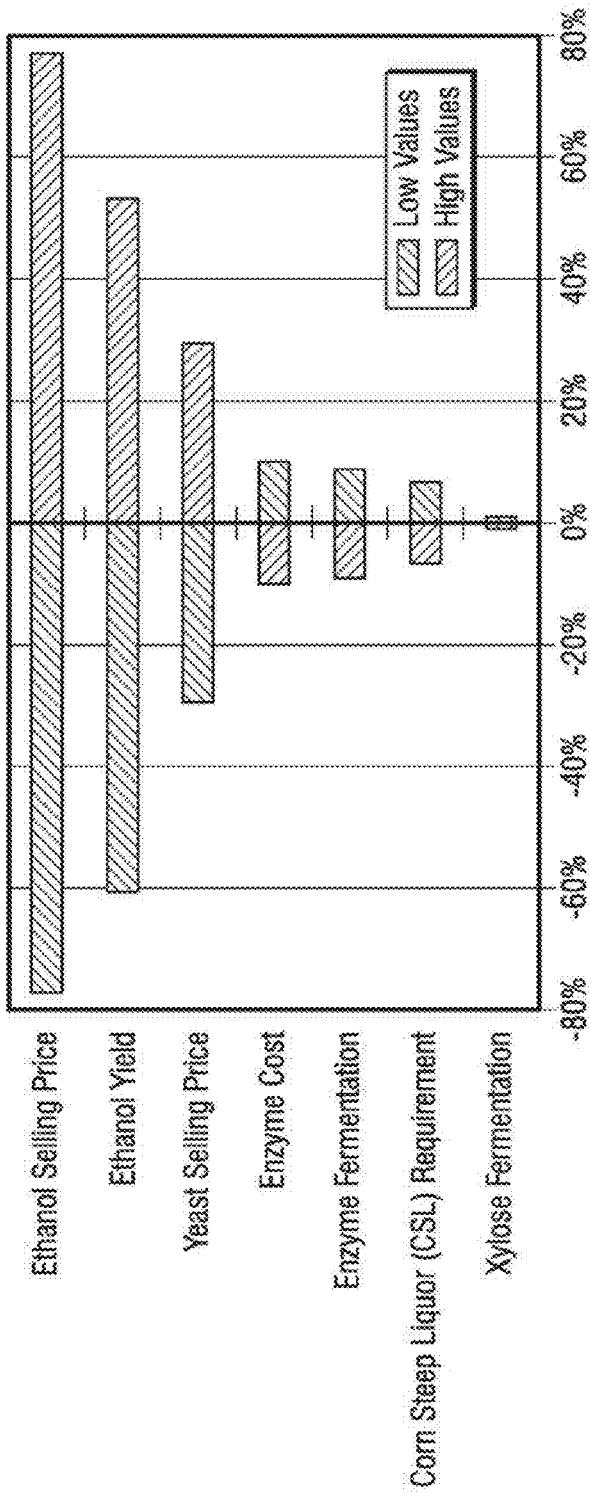
FIG. 20B shows a sensitivity analysis in an embodiment of the present invention.

FIG. 15 shows in-house enzyme production using AFEX-pretreated corn stover in an embodiment of the present invention.
   FIG. 16 provides relevant conclusions pertinent to one or more of FIGS. 11A, 11B, 12, 13, 14A, 14B and 15 in embodiment of the present invention.
   FIG. 17A shows a first portion of an exemplary fermentation process in an embodiment of the present invention.
   FIG. 17B shows a second portion of an exemplary fermentation process in an embodiment of the present invention.
   FIG. 18 shows a graph of xylose concentration over time in embodiments of the present invention.
   FIG. 19 provides relevant conclusions pertinent to one or more of FIGS. 17A, 17B and 18 in embodiments of the present invention.
   FIG. 20A shows a comparison cost/revenue study in an embodiment of the present invention.
   FIG. 20B shows a sensitivity analysis in an embodiment of the present invention.

Additional Conclusions

Nutrients inherently from corn stover are sufficient to support microbial growth for fermentation. Exogenous nutrients are not required.

85% of the carbohydrate was solubilized at 18% solids loading. The sugar concentration could produce ethanol at 55 g/L.

In-house enzyme production reduced the exogenous enzyme requirement from 10 mg/g CS to 1.0 mg/g CS (10 fold reduction). The overall cost of enzyme reduced primarily due to the ability to utilize sugars (both monomers and oligomers) from AFEX-CS for enzyme production.

High cell density fermentation can be conducted without the need for high fresh cell inoculum due to the high recyclability of yeast cells in the hydrolysate.

Compared to base case (Eggeman and Elander, 2005), the total profit is expected to increase from 1.2 to 35.2 USD/Mg feedstock largely due to the value of non-GM yeast cells and reduction in enzyme cost.

REFERENCES

All publications, patents and patent documents are incorporated by reference herein, each in their entirety, as though individually incorporated by reference. In the case of any inconsistencies, the present disclosure, including any definitions therein, will prevail.

Eggeman T. and Elander R. Process and economic analysis of pretreatment technologies. Bioresource Technology 96, 2019-2025 (2005)

Walker, G. M., 2004. Metals in Yeast Fermentation Processes. in: A. I. Laskin, J. W. Bennet, G. M. Gadd (Eds.), Advances in Applied Microbiology. Elsevier Academic Press, New York, N.Y.

Lau, M. W., Dale, B. E., 2009. Cellulosic ethanol production from AFEX-treated corn stover using *Saccharomyces cerevisiae* 424A (LNH-ST). Proc Natl Acad Sci USA, 106, 1368-73.

Example 3

Prophetic

Additional testing with other biomass materials, such as switch grass and poplar will be performed. It is expected that the aqueous extract will stimulate the growth and performance of potential consolidated bioprocessing organisms such as *Clostridium thermocellum*.

Conclusion

The various embodiments described herein provide for developing microbial growth stimulants from mildly alkaline aqueous extracts from AFEX treated biomass. In one embodiment, a method comprising extracting solubles from pretreated lignocellulosic biomass (e.g., corn stover) using water and an aqueous extract as a growth medium for the cellulase enzyme-producing fungus (*T. reesei*), is provided. In one embodiment, the pretreated lignocellulosic biomass is ammonia fiber expansion pretreated lignocellulosic biomass.

The experimental results show that the integrated recovery of sugar and protein from early cut switchgrass appears to be a feasible approach to a cellulosic biorefinery. Ammonium hydroxide has been shown to be an effective solvent for removing proteins from the biomass, thus opening up possibilities of integrating with AFEX pretreatment or providing a nitrogen source during fermentation. Integrating sugar and protein production will cause some tradeoffs, as producing maximum sugar will result in a lower protein recovery and vice versa. However, there are possibilities for overcoming these obstacles.

Further integration of these two (2) steps is also possible. If the loss in sugar yields is due solely to oligomer loss, then using the protein extract as the hydrolysate liquid after separating the proteins would reduce these losses. This would require neutralizing the extract, but would decrease overall water use and thereby improve the environmental and economic performance of the refinery. In addition, the fact that there are multiple protein streams may allow further specialization. If the cellulase enzymes are still active after hydrolysis, it may be possible to concentrate and recycle them, again reducing operating costs.

Embodiments of the invention described herein provide for collecting the protein content found within grasses and optionally as those proteins added during cellulose and hemicellulose hydrolysis using dilute ammonium hydroxide as the solvent. These proteins are captured in two steps: the initial hydrolysis of the carbohydrates and a separate extraction step where the order is dictated by economics. Thus, proteins are recovered from the hydrolysate before or after the carbohydrates are fermented. The remaining biomass after fermentation then undergoes a simulated crossflow extraction to remove any remaining proteins.

This is the first method to use ammonium hydroxide as a solvent, which has two (2) advantages over the previous approaches. Firstly, any residual ammonia remaining on the final protein product used as a feed for ruminants provides extra nitrogen in its diet, thereby improving the overall crude protein content of the final product. Other alkaline solutions could provide a negative effect due to the presence of unwanted ions, such as sodium. Secondly, ammonia is also used during the Ammonia Fiber Expansion (AFEX) pretreatment process. Thus, the ammonia used for extraction can be taken from the ammonia recovery system in place for the AFEX process, and then recycled back into AFEX after concentrating the proteins. Thus, using ammonia for extraction eliminates the need for an additional reagent.

The process can remove over 99% of the proteins from the solid biomass, indicating a very high recovery is possible. Extracting proteins from untreated switchgrass provides yields of approximately 35%. By using a separate extraction step after hydrolysis, it is possible to recover not only the proteins still remaining within the biomass, but also those that are adsorbed onto the biomass surface. In addition, the disruption of the biomass' structure during the AFEX pretreatment process and the carbohydrate hydrolysis improves the diffusion of proteins from the solid into solution. No other process has focused on combining protein extraction with AFEX and carbohydrate hydrolysis.

With two (2) separate protein streams, there exists the possibility that they can be used for separate purposes. For example, the stream containing the enzymes required for hydrolysis can be recycled, thus reducing the overall cost of carbohydrate production. The other proteins within that stream would bind to the lignin present, deactivating those sites and preventing the enzymes from binding to them. This could potentially increase the rate of hydrolysis, further reducing the cost to the refinery.

A simulated crossflow extraction is used to increase the overall amount of proteins extracted while still keeping solvent use low. The biomass is put through a number of extractions while still maintaining a small solvent use by using the same solvent for subsequent extractions, as only the final extraction uses fresh solvent. This not only reduces the cost of extraction, but also the costs to concentrate the proteins downstream.

In one embodiment, this process is useful for a cellulosic ethanol production facility, as it could provide a valuable co-product to ethanol. These proteins can be sold as animal feed, serving as a substitute for soy protein. In addition, it is possible to apply this method to transgenic biomass engineered to produce specific industrial or pharmaceutical enzymes, as described in U.S. application Ser. No. 11/489,234, filed Jul. 19, 2006, and U.S. Pat. No. 7,049,485 which are commonly owned by the Assignee and which are incorporated herein by reference in their entireties.

This method can be implemented in line with cellulose hydrolysis. No changes would be necessary for either the AFEX process or the hydrolysis reaction chamber. The solids and liquids must be separated after hydrolysis, either through centrifugation or standard filtration. The liquid stream then can pass through a crossflow ultrafiltration system, allowing the sugars and most of the water to pass through, leaving behind a concentrated protein product.

A simulated crossflow extraction would need to be implemented for the remaining solid material. The solids would pass through three (3) separate extraction vessels, where they would be mixed with the incoming ammonium hydroxide. The solids and liquids will need to be separated between each step, again through either centrifugation or filtration. After the solvent undergoes its final extraction step, it must also be concentrated. It can be combined with the liquid stream from the hydrolysate or be concentrated through a separate crossflow ultrafiltration step.

The remaining ammonium hydroxide solution can then be recycled into the AFEX ammonia recovery system. It may be necessary to remove any organic matter still remaining in solution before this step. A simple distillation column can remove the volatile ammonia, concentrating and separating it from the solubilized biomass. This stream can then be recovered, while the remaining liquid can be sent elsewhere for waste treatment or further processing.

Alternative embodiments are also available, depending on how integrated one wishes this process to be. Rather than recycling the ammonia into the AFEX recovery process, a separate recycle stream for the extraction process can be used. If the extraction is performed prior to hydrolysis, the ammonium hydroxide solution can also be neutralized and used as the hydrolysate media as well. A standard one or two step extraction process can replace the simulated crossflow extraction.

Cellulosic biomass contains large amounts of structural carbohydrates (cellulose, hemicellulose, etc.) that might provide much less expensive sugars for fermentation or non-biological transformation to a variety of products or as improved animal feeds. Such biomass also contains smaller but nonetheless significant amounts of proteins and other solubles such as simple sugars, lipids and minerals. These less abundant components can be separated from the structural carbohydrates as part of a larger "biorefining" process. Recovering these soluble components during biorefining reduces the amount of waste that must be handled by the biorefinery and would also help provide additional valuable products that could improve the economic feasibility of the overall biorefining process. In addition, plants may be genetically engineered to produce various molecules that might be separated and recovered from herbaceous biomass in this way.

Embodiments described herein allow for extraction and utilization of virtually all solubles in herbaceous biomass, not just protein. The embodiments can further utilize substantially all types of herbaceous biomass, including both wet and dry biomass, not just freshly harvested materials; (3) the various embodiments integrate easily and naturally into a larger process using concentrated ammonia to treat biomass to enhance the conversion of cellulose and hemicellulose to sugars; (4) the conditions of solubles recovery (pH and temperature) can preserve much of the value of fragile molecules, including proteins; and (5) the ability to separate and upgrade these solubles to make salable products avoids the expense and other difficulties associated with treating them as wastes, and may significantly improve the economic "bottom line" of the overall process.

Markets that might use the various embodiments of this invention include, but are not limited to: (1) the U.S. chemical industry which is beginning to move away from petroleum as a source of chemical feedstocks and is interested in inexpensive sugars as platform chemicals for new, sustainable processes; (2) the fermentation industry, especially the fuel ethanol production industry which is also interested in inexpensive sugars from plant biomass; (3) the animal feed industry which is strongly affected by the cost of protein and other nutrients for making animal feeds of various kinds; and (4) the fertilizer industry that may utilize the minerals that will result from solubles extraction.

In one embodiment, the steps are generally:

(1) Following pretreatment of herbaceous biomass with concentrated ammonia: water mixtures in an AFEX process to disrupt the chemical and physical structure of biomass.

(2) Soak the pretreated biomass in warm (up to 80° C.), alkaline (up to pH 10) aqueous solutions of ammonium hydroxide in water, using approximately 5-15 mass units of water per mass of dry biomass.

(3) Allow sufficient time for the desired level of extraction to occur under these conditions, but less than 1 hour.

(4) Using appropriate filtration equipment, remove the liquid from the solids.

(5) Acidify the liquid to about pH 5.0 or thereabouts and/or heat the liquid stream to precipitate proteins and other less soluble components.

(6) Recover and separate these proteins and associated solubles by appropriate combinations of washing, drying and ultrafiltration.

(7) Treat the residual liquid remaining after protein precipitation or separation to prepare it to serve as a microbial growth stimulant.

(8) Enzymatically hydrolyze the residual solids from which these proteins were extracted to release simple sugars for fermentation and treat the resulting liquid to recover additional protein and other non-sugar solubles if the concentrations of these species warrant it. Efficient, mature biomass refining to fuels and chemicals requires complete utilization of all components of the biomass, including protein and other solubles. These additional products help improve the overall economics of biomass refining and avoid the costs associated with treating these components as wastes if they are not recovered in useful products.

Lignocellulosic biomass, especially herbaceous biomass, contains significant amounts of protein and other solubles. This invention addresses the opportunity to integrate recovery of solubles such as protein in an overall biomass refining system. Warm solutions of ammonia and water are used to extract this protein and other solubles from biomass. The extracted species are recovered and sold as additional products from the biorefinery, thereby increasing profits and reducing the amount of waste that would otherwise be treated.

In one embodiment, the process particularly enables production of Microbial Growth Stimulants (MGSs) as follows:

After an AFEX treatment, extract protein rich solutions from herbaceous biomass at slightly alkaline pH (pH 7 to 10) using ammonia at moderate temperatures (50-80° C.).

(1) Recover ammonia from this protein rich solution to the extent desired via stripping with inert gases (for example, nitrogen), heating, etc. The objective is to leave ammonia in the solution at the level desired in the ultimate MGS product.

(2) Recover most of the protein from this solution by appropriate combinations of heating and pH adjustment. Heating may be accomplished, for example, by direct injection of steam into the extracted liquid while pH adjustment may be accomplished by bubbling carbon dioxide (an acid gas) through the liquid or by addition of a mineral acid such as sulfuric acid.

(3) Depending on the ultimate use and desired purity of the protein product, proteins may also be recovered by membrane separation, for example by ultrafiltration or reverse osmosis techniques.

(4) The liquid remaining following protein recovery is the MGS product. It can be used directly in fermentation processes within the same plant in which the MGS is produced, as a liquid supplement to animal feeds for animals fed in close proximity to the plant, or it can be concentrated by multieffect evaporation and sold in more distant feed and fermentation markets. Sufficiently inexpensive sugars from renewable plant biomass could become the basis of a very large chemical and fuels industry, replacing or substituting for petroleum and other fossil feedstocks. Much of this renewable carbon based industry would use microbial fermentation as the preferred means of generating fuels and chemicals from plant biomass. Microbial Growth Stimulants (MGSs) such as Corn Steep Liquor (CSL) are widely used to increase the rate and yield of many fermentation processes. If a very large scale fermentation industry for fuels and chemicals from plant matter develops in the future, supplies of CSL will not be adequate to the need and prices will be excessive. A new generation of Microbial Growth Stimulants (MGS) is described based on liquid streams remaining after protein is extracted and recovered from herbaceous biomass such as grasses and hays. These MGSs are rich in protein, non protein nitrogen, soluble sugars, vitamins, and minerals.

REFERENCES

All publications, patents and patent documents are incorporated by reference herein, each in their entirety, as though individually incorporated by reference. In the case of any inconsistencies, the present disclosure, including any definitions therein, will prevail.

1. Lin, Y. and Tanaka, S. (2006), Appl. Microbiol. Biotechnol. 69, 627-642.
2. Greene, N. (2003), Growing Energy, Natural Resources Defense Council.
3. Sanders on, M. A., Reed, R. L., McLaughlin, S. B., Wullschleger, S. D., Conger, B. V., and Parrish, D. J. (1996) Bioresour. Technol. 56, 83-93.
4. Mosier, N., Wyman, C., Dale, B., Elander, R., Lee, Y., Holtzapple, M., and Ladisch, M. (2005), Bioresour. Technol. 96, 673-686.
5. Sulbaran-de-Ferrer, B., Aristiguieta, M., Dale, B., Ferrer, A., and Ojeda-de-Rodriguez, G. (2003), Appl. Biochem. and Biotechnol. 105-108, 155-164.
6. Teymouri, F., Laureano-Perez, L., Alizadeh, H., and Dale, B. (2005), Bioresource Technology 96, 2014-2018.
7. Holtzapple, M., Jun, J., Ashok, G., Patibandla, S., Dale, B. (1991), Appl. Biochem. and Biotechnol. 28-29, 59-74.
8. Ferrer, A., Byers, F. M., Sulbarán De Ferrer, B., Dale, B. E., and Aiello, C. (2000), Appl. Biochem. and Biotechnol. 84-86, 163-179.
9. Alizadeh, H., Teymouri, F., Gilbert, T., and Dale, B. (2005), Appl. Biochem. and Biotechnol. 121-124, 1133-1141.
10. Ordonez, C., Asenjo, M., Benitez, C., and Gonzalez, J. (2001), Bioresour. Technol. 78, 187-190.
11. Lawhon, J. (1986), U.S. Pat. No. 4,624,805. Nov. 25, 1986.
12. El-Adaway, T., Rahma, E., El-Bedawey, A., and Gafar, A. (2001), Food Chem. 74, 455-462.
13. Park, S. and Bean, S. (2003), J. Agric. Food Chem. 51, 7050-7054.
14. Betschart, A. and Kinsella J. (1973), J. Agric Food Chem., 21(1), 60-65.
15. Fernandez, S., Padilla, A., Mucciarelli, S. (1999), Plant Foods for Human Nutrition 54, 251-259.
16. Fiorentini, R. and Galoppini, C. (1981), J. Food Sci. 46, 1514-1520.
17. De La Rosa, L. B., Reshamwala, S., Latimer, V., Shawky, B., Dale, B., and Stuart, E. (1994), Appl. Biochem. and Biotechnol. 45-46, 483-497.
18. Urribarri, L., Ferrer, A., and Colina, A. (2005), Appl. Biochem. and Biotechnol. 121-124, 721-730.
19. NREL (2004), Chemical Analysis and Testing (CAT) Standard Procedures, National Renewable Energy Laboratory.
20. Lovrien, R. and Matulis, D. (1995), Current Protocols in Protein Science, 3.4.1-3.4.24.
21. Madakadze, I., Stewart, K., Peterson, P., Coulman, B., and Smith, D. (1999) Crop Sci. 39, 552-557.
22. Allan, G., Parkinson, S., Booth, M., Stone, D., Rowland, S., Frances, J., and Warner-Smith, R. (1999), Aquaculture 186, 293-310.

Although specific embodiments have been illustrated and described herein, it will be appreciated by those of ordinary skill in the art that any arrangement that is calculated to achieve the same purpose may be substituted for the specific embodiment shown. This application is intended to cover any adaptations or variations of the present subject matter. Therefore, it is manifestly intended that embodiments of this invention be limited only by the claims and the equivalents thereof.

What is claimed is:

1. A method for producing a microbial growth stimulant solution from a lignocellulosic plant biomass comprising:
providing a harvested lignocellulosic plant biomass;
treating the plant biomass with an Ammonia Fiber Explosion (AFEX) process to provide a treated plant biomass;
soaking the treated plant biomass in an alkaline aqueous solution of ammonium hydroxide at 25° to 70° C. to provide a soaked plant biomass in the solution;
extracting the solution from the soaked plant biomass to produce an extracted solution;
separating at least some of the proteins and ammonia from the extracted solution; and
retaining the extracted solution as the microbial growth stimulant solution.

2. The method of claim 1 wherein the plant is a monocot.

3. The method of claim 2 wherein the monocot is switchgrass, rice or maize.

4. The method of claim 1 wherein the plant biomass is switchgrass.

5. The method of claim 1 wherein a pH in the soaking step is above about 8.

6. The method of claim 1 wherein the proteins are separated from the extracted solution by precipitation or ultrafiltration.

7. The method of claim 1 wherein the separating step occurs after a hydrolysis step.

8. The method of claim 1 wherein the separating step occurs before a hydrolysis step.

9. The method of claim 1 wherein the aqueous alkaline ammonium hydroxide solution comprises up to about 3% by weight $NH_4OH$.

10. The method of claim 9 wherein the aqueous alkaline ammonium hydroxide solution has a pH greater than about 8.

11. The method of claim 1 wherein no nutrients are added to the plant biomass.

12. The method of claim 1 wherein the extracted solution is extracted with water.

* * * * *